US011463629B2

(12) United States Patent
Miyai et al.

(10) Patent No.: US 11,463,629 B2
(45) Date of Patent: Oct. 4, 2022

(54) MEDICAL SYSTEM, MEDICAL APPARATUS, AND CONTROL METHOD

(71) Applicant: Sony Corporation, Tokyo (JP)

(72) Inventors: Takeshi Miyai, Kanagawa (JP);
Yasuaki Takahashi, Kanagawa (JP);
Masahito Yamane, Kanagawa (JP);
Yuki Sugie, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/614,387

(22) PCT Filed: Mar. 16, 2018

(86) PCT No.: PCT/JP2018/010435
§ 371 (c)(1),
(2) Date: Nov. 18, 2019

(87) PCT Pub. No.: WO2018/230066
PCT Pub. Date: Dec. 20, 2018

(65) Prior Publication Data
US 2020/0077012 A1      Mar. 5, 2020

(30) Foreign Application Priority Data

Jun. 12, 2017 (JP) .............................. JP2017-115019

(51) Int. Cl.
*H04N 5/235* (2006.01)
*H04N 5/225* (2006.01)
(52) U.S. Cl.
CPC ......... *H04N 5/2355* (2013.01); *H04N 5/2256* (2013.01); *H04N 5/2351* (2013.01); *H04N 2005/2255* (2013.01)
(58) Field of Classification Search
CPC .. H04N 5/2355; H04N 5/2256; H04N 5/2351; H04N 5/2255; H04N 2005/2255;
(Continued)

(56) References Cited

U.S. PATENT DOCUMENTS

2010/0045824 A1    2/2010   Kido et al.
2014/0275764 A1*   9/2014   Shen .................. A61B 1/00009
                                              600/103
(Continued)

FOREIGN PATENT DOCUMENTS

CN      105473049 A     4/2016
CN      106659371 A     5/2017
(Continued)

OTHER PUBLICATIONS

Extended European Search Report dated May 11, 2020, issued in corresponding European Application No. 18817411.4, 9 pages.

(Continued)

*Primary Examiner* — Michael E Teitelbaum
(74) *Attorney, Agent, or Firm* — Xsensus, LLP

(57) ABSTRACT

It is desired to provide a technology which is capable of reducing glare to be felt by a user for an output image by an HDR monitor in a case where an image is caused to be displayed at the HDR monitor on the basis of an HDR image.

There is provided a medical system including a light source configured to irradiate a subject inside a living organism; an imaging unit configured to image the subject coaxially with an optical axis of the light source; and a control unit configured to control the light source and the imaging unit, in which the control unit performs control so that a signal compliant with high-dynamic range standards is output by adjusting gradation for a first image signal acquired by the imaging unit.

20 Claims, 23 Drawing Sheets

(58) Field of Classification Search
CPC ...... H04N 5/2356; H04N 5/20; H04N 5/2354; H04N 7/18; A61B 1/000095; A61B 1/0655; A61B 1/018; A61B 1/043; A61B 1/0638; A61B 1/313; A61B 1/045; G09G 2320/0271; G09G 2320/0673; G09G 5/10; G09G 2340/02; G09G 2340/0428; G09G 2380/08; G02B 21/36; G02B 23/24

See application file for complete search history.

(56) References Cited

U.S. PATENT DOCUMENTS

| | | | |
|---|---|---|---|
| 2017/0061894 A1* | 3/2017 | Ikeda | G09G 5/006 |
| 2017/0084067 A1* | 3/2017 | Son | H04N 21/00 |

FOREIGN PATENT DOCUMENTS

| | | |
|---|---|---|
| JP | 03-037037 A | 2/1991 |
| JP | 2000-023183 A | 1/2000 |
| JP | 2009-297133 A | 12/2009 |
| JP | 2011-123175 A | 6/2011 |
| JP | 2013-042998 A | 3/2013 |
| JP | 2014-524290 A | 9/2014 |
| JP | 2016-538008 A | 12/2016 |
| WO | 2013025530 A1 | 2/2013 |
| WO | 2016/129160 A1 | 8/2016 |
| WO | 2017/002544 A1 | 1/2017 |
| WO | 2017/073302 A1 | 5/2017 |

OTHER PUBLICATIONS

International Search Report and Written Opinion dated Jun. 12, 2018 for PCT/JP2018/010435 filed on Mar. 16, 2018, 10 pages including English Translation of the International Search Report.

Sharp, "Release of monitor corresponding to 70 inch 8K HDR", Retrieved from Internet URL: http://www.optronics-media.com/news/20170412/46372/ on May 29, 2018.

\* cited by examiner

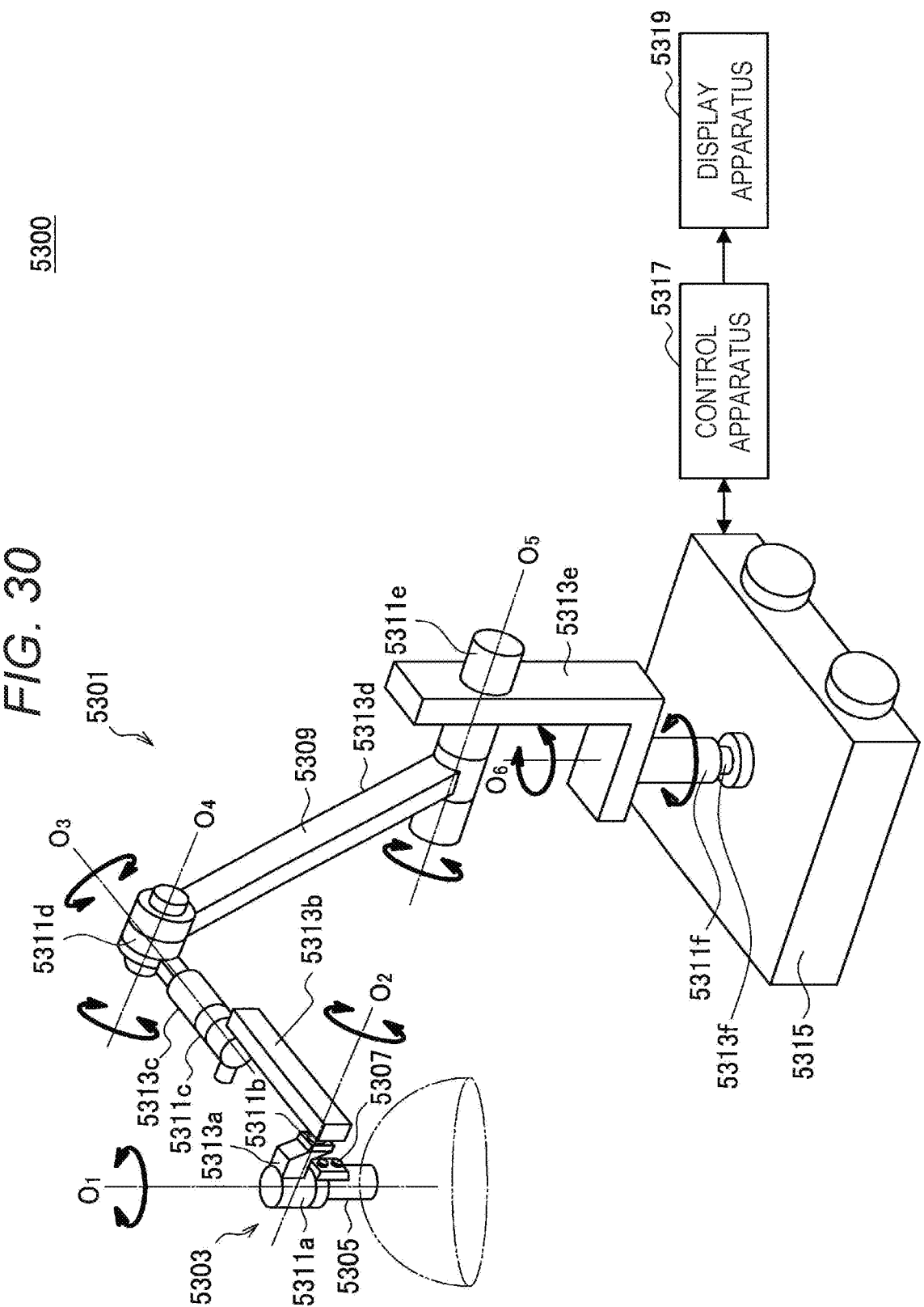

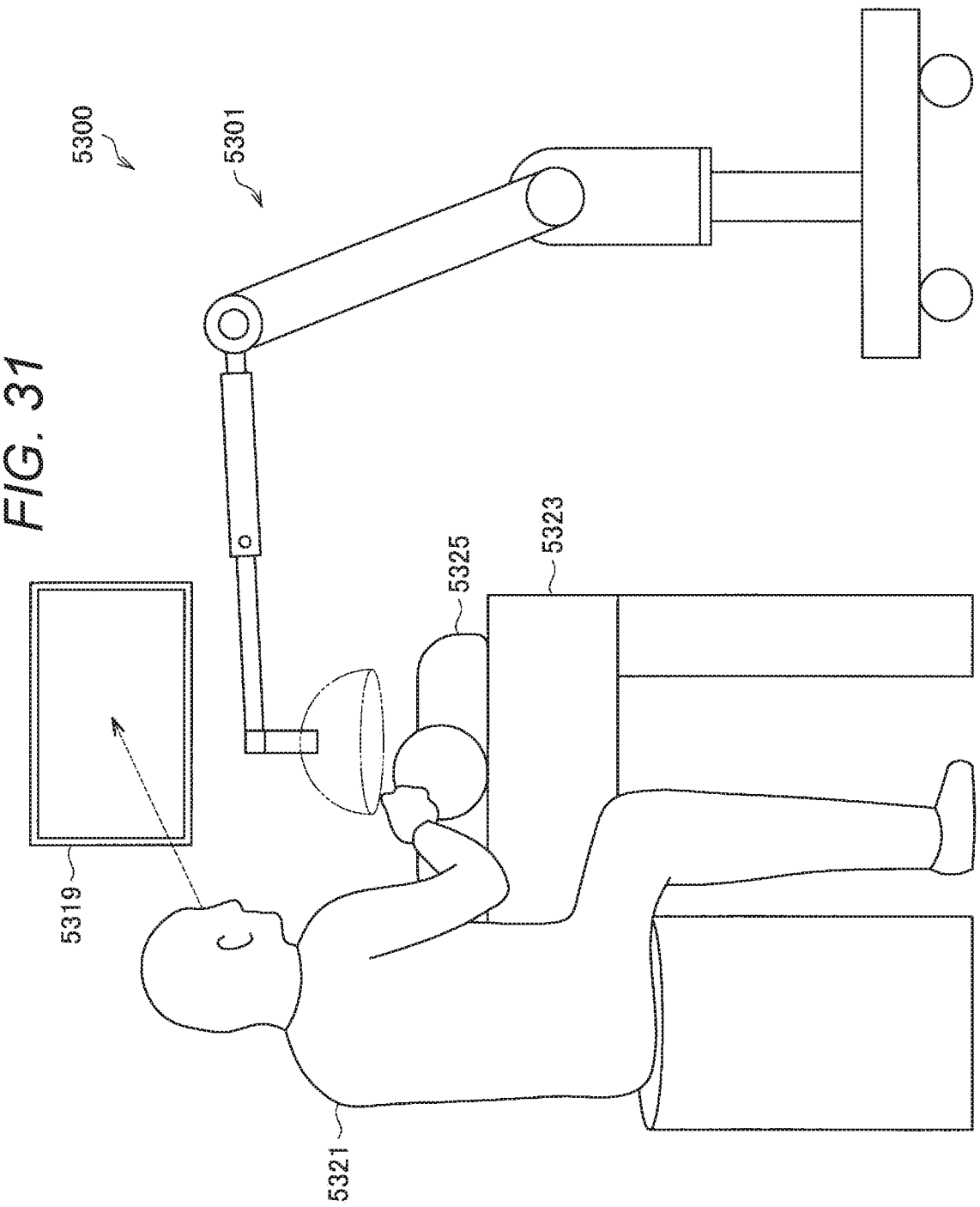

MEDICAL SYSTEM, MEDICAL APPARATUS, AND CONTROL METHOD

CROSS-REFERENCE TO RELATED APPLICATIONS

The present application is based on PCT filing PCT/JP2018/010435, filed Mar. 16, 2018, which claims priority to JP 2017-115019, filed Jun. 12, 2017, the entire contents of each are incorporated herein by reference.

TECHNICAL FIELD

The present disclosure relates to a medical system, a medical apparatus and a control method.

BACKGROUND ART

In recent years, an endoscope is sometimes used in medical practice. In a case where imaging is performed using an endoscope, imaging is generally performed by illumination light being radiated from the front on a subject which exists in a short distance and which has a depth. Therefore, an image captured with the endoscope (hereinafter, also referred to as an "endoscope image") has characteristics that halation is likely to occur on a front side of the subject, and blocked-up shadow is likely to occur on a back side of the subject and at a portion of shadow on the subject.

Such a phenomenon can occur in a similar manner also in a case where various medical apparatuses are used in medical practice such as in a case where a microscope is used, as well as in a case where an endoscope is used. As a method for reducing such halation and blocked-up shadow, there is a technology of acquiring a high dynamic range (HDR) image, in which information of a wide brightness range from a dark portion to a bright portion is acquired (see, for example, Patent Document 1).

However, a monitor which displays an image is generally a monitor which can express a brightness range narrower than a brightness range of the HDR image which is acquired as described above. In the following description, a brightness range narrower than the brightness range of the HDR image will be also referred to as a "standard dynamic range (SDR)". Typically, instead of the HDR image itself being output to an SDR monitor, after gradation of the HDR image acquired as described above is compressed and converted into an SDR image, the SDR image is output to the SDR monitor. However, in such a case, it is not possible to sufficiently utilize abundant brightness information of the HDR image.

Meanwhile, in recent years, an HDR monitor which can display information in a wide brightness range from a dark portion to a bright portion has been developed. Therefore, by outputting an HDR image to an HDR monitor with brightness as is without gradation compression being performed for the HDR image acquired as described above, it is possible to sufficiently utilize abundant brightness information of the HDR image.

CITATION LIST

Patent Document

Patent Document 1: Japanese Patent Application Laid-Open No. 2000-23183

SUMMARY OF THE INVENTION

Problems to be Solved by the Invention

However, on the other hand, in a case where an HDR image acquired with an endoscope is displayed at an HDR monitor with brightness as is, there is a case where a user feels glare for a portion on a front side intensely illuminated with illumination light, a portion which is extremely bright by specular reflection among the displayed HDR image, and the like. Further, particularly, in diagnosis or surgery using an endoscope, a surgeon gets uncomfortable by continuously watching these HDR images for a long period of time, which may become hindrance of implementation of diagnosis or surgery.

Therefore, it is desired to provide a technology which is capable of reducing glare to be felt by a user for an output image by an HDR monitor in a case where an image is caused to be displayed at the HDR monitor on the basis of an HDR image.

Solutions to Problems

According to the present disclosure, there is provided a medical system including a light source configured to irradiate a subject inside a living organism; an imaging unit configured to image the subject coaxially with an optical axis of the light source; and a control unit configured to control the light source and the imaging unit, in which the control unit performs control so that a signal compliant with high-dynamic range standards is output by adjusting gradation for a first image signal acquired by the imaging unit.

According to the present disclosure, there is provided a medical apparatus including a control unit configured to perform control to image a subject inside a living organism to acquire a first image signal, generate a second image signal having a first dynamic range compliant with high-dynamic range standards on the basis of the first image signal, generate a third image signal for which a difference between a maximum value of brightness and a minimum value of brightness is smaller than the first dynamic range on the basis of the first image signal, and output the second image signal or the third image signal.

According to the present disclosure, there is provided a medical apparatus including a control unit configured to control a light source which irradiates a subject inside a living organism and an imaging unit which images the subject coaxially with an optical axis of the light source, in which the control unit performs control to output a signal compliant with high-dynamic range standards by adjusting gradation for a first image signal acquired by the imaging unit.

According to the present disclosure, there is provided a control method including controlling a light source which irradiates a subject inside a living organism and an imaging unit which images the subject coaxially with an optical axis of the light source, and performing control to output a signal compliant with high-dynamic range standards by adjusting gradation for a first image signal acquired by the imaging unit.

Effects of the Invention

As described above, according to the present disclosure, a technology is provided which is capable of reducing glare to be felt by a user for an output image by an HDR monitor in a case where an image is caused to be displayed at an HDR monitor on the basis of an HDR image. Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 30 is a view illustrating an example of a schematic configuration of a microscopic surgery system.

FIG. 31 is a view illustrating aspect of surgery using the microscopic surgery system illustrated in FIG. 30.

MODE FOR CARRYING OUT THE INVENTION

Figure 1:
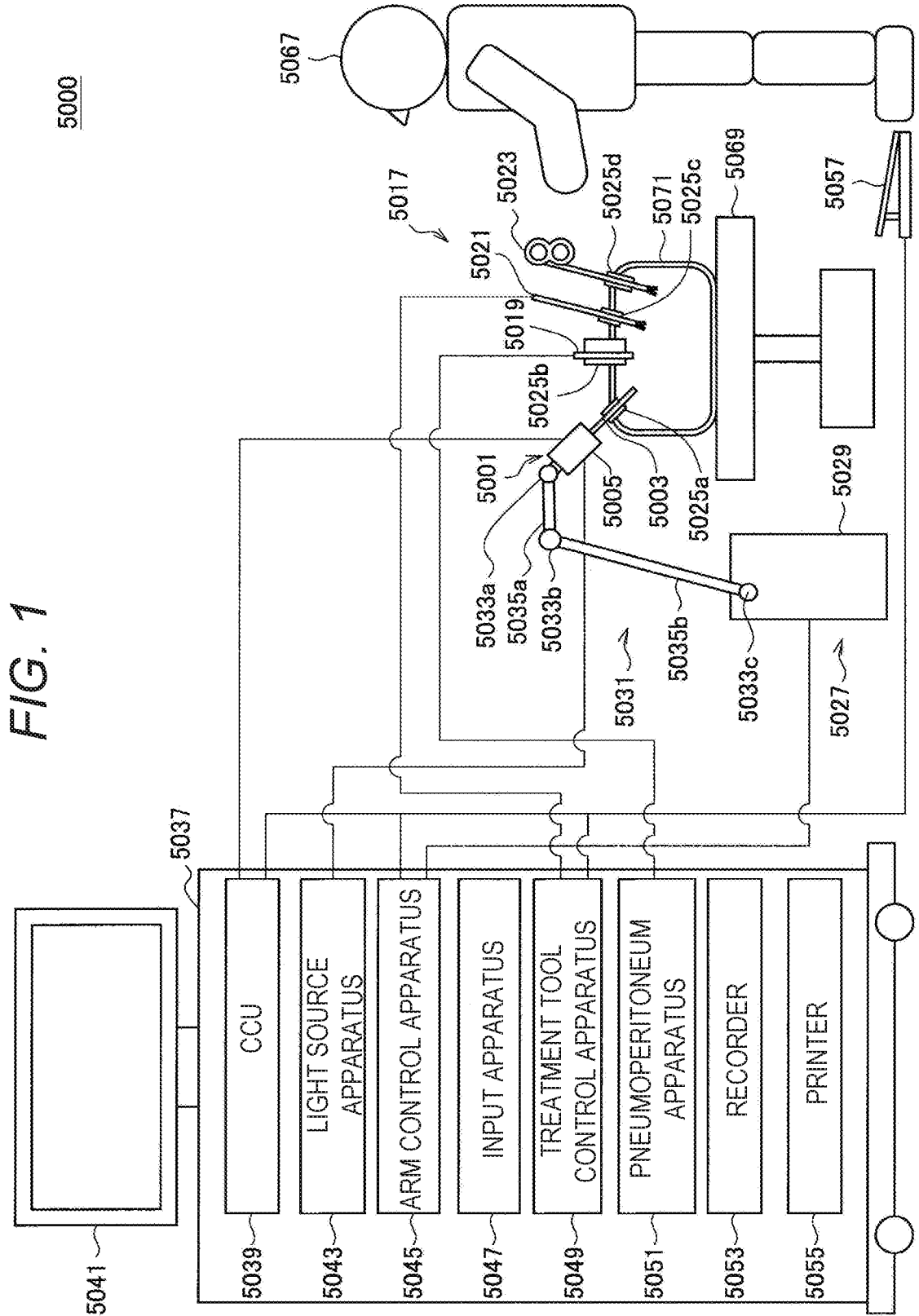
FIG. 1 is a view illustrating an example of a schematic configuration of an endoscopic surgery system.

Hereinafter, a preferred embodiment of the present disclosure will be described in detail with reference to the appended drawings. Note that, in this specification and the appended drawings, structural elements that have substantially the same functional configuration are denoted with the same reference numerals, and repeated explanation of these structural elements is omitted.

In addition, in this specification and the drawings, a plurality of structural elements that have substantially the same or similar functional configuration are sometimes distinguished from each other using different numbers after the same reference numerals. However, in the case where there is no need in particular to distinguish the plurality of structural elements that have substantially the same or similar functional configuration, the same reference numeral alone is attached. In addition, similar structural elements according to different embodiments are sometimes distinguished from each other using different alphabets after the same reference numerals. However, in the case where there is no need in particular to distinguish such similar structural elements, the same reference numeral alone is attached.

Note that description will be provided in the following order.

1. System Configuration Example
2. Outline
3. Basic Configuration
4. Embodiments
   4.1. First embodiment
   4.2. Second embodiment
   4.3. Third embodiment
   4.4. Fourth embodiment
   4.5. Fifth embodiment
   4.6. Sixth embodiment
   4.7. Seventh embodiment
   4.8. Eighth embodiment
5. Application example
6. Conclusion

1. System Configuration Example

First, a configuration example of an example of a medical system according to an embodiment of the present disclosure will be described with reference to the drawings. Various systems are assumed as an example of the medical system according to the embodiment of the present disclosure. Here, a configuration example of an endoscopic surgery system will be mainly described as an example of the medical system according to the embodiment of the present disclosure.

FIG. 1 is a view illustrating an example of a schematic configuration of an endoscopic surgery system 5000 to which the technology according to an embodiment of the present disclosure can be applied. In FIG. 1, a state is illustrated in which a surgeon (medical doctor) 5067 is using the endoscopic surgery system 5000 to perform surgery for a patient 5071 on a patient bed 5069.

As illustrated, the endoscopic surgery system 5000 includes an endoscope 5001, other surgical tools 5017, a support arm apparatus 5027 which supports the endoscope 5001 thereon, and a cart 5037 on which various apparatus for endoscopic surgery are mounted.

In endoscopic surgery, in place of incision of the abdominal wall to perform laparotomy, a plurality of tubular aperture devices called trocars 5025a to 5025d is used to puncture the abdominal wall. Then, a lens barrel 5003 of the endoscope 5001 and the other surgical tools 5017 are inserted into body cavity of the patient 5071 through the trocars 5025a to 5025d. In the example illustrated, as the other surgical tools 5017, a pneumoperitoneum tube 5019, an energy device 5021 and forceps 5023 are inserted into body cavity of the patient 5071. Further, the energy device 5021 is a treatment tool for performing incision and peeling of a tissue, sealing of a blood vessel or the like by high frequency current or ultrasonic vibration. However, the surgical tools 5017 illustrated are mere examples at all, and as the surgical tools 5017, various surgical tools which are generally used in endoscopic surgery such as, for example, tweezers or a retractor may be used.

An image of a surgical region in a body cavity of the patient 5071 imaged by the endoscope 5001 is displayed on a display apparatus 5041. The surgeon 5067 would use the energy device 5021 or the forceps 5023 while watching the image of the surgical region displayed on the display apparatus 5041 on the real time basis to perform such treatment as, for example, resection of an affected area or the like. It is to be noted that, though not illustrated, the pneumoperitoneum tube 5019, the energy device 5021 and the forceps 5023 are supported by the surgeon 5067, an assistant or the like during surgery.

(Support Arm Apparatus)

The support arm apparatus 5027 includes an arm unit 5031 extending from a base unit 5029. In the example illustrated, the arm unit 5031 includes joint units 5033a, 5033b and 5033c and links 5035a and 5035b and is driven under the control of an arm control apparatus 5045. The endoscope 5001 is supported by the arm unit 5031 such that the position and the posture of the endoscope 5001 are controlled. Consequently, stable fixation in position of the endoscope 5001 can be implemented.

(Endoscope)

The endoscope 5001 includes the lens barrel 5003 which has a region of a predetermined length from a distal end thereof to be inserted into a body cavity of the patient 5071, and a camera head 5005 connected to a proximal end of the lens barrel 5003. In the example illustrated, the endoscope 5001 is illustrated as a so-called rigid endoscope having the lens barrel 5003 of the hard type. However, the endoscope 5001 may otherwise be configured as a so-called flexible endoscope having the lens barrel 5003 of the flexible type.

The lens barrel 5003 has, at a distal end thereof, an opening in which an objective lens is fitted. A light source apparatus 5043 is connected to the endoscope 5001 such that light generated by the light source apparatus 5043 is introduced to a distal end of the lens barrel by a light guide extending in the inside of the lens barrel 5003 and is irradiated toward an observation target in a body cavity of the patient 5071 through the objective lens. It is to be noted that the endoscope 5001 may be a forward-viewing endoscope or may be an oblique-viewing endoscope or a side-viewing endoscope.

An optical system and an imaging element are provided in the inside of the camera head 5005 such that reflected light (observation light) from an observation target is condensed on the imaging element by the optical system. The observation light is photo-electrically converted by the imaging element to generate an electric signal corresponding to the observation light, namely, an image signal corresponding to an observation image. The image signal is transmitted as RAW data to a camera control unit (CCU) 5039. It is to be noted that the camera head 5005 has a function incorporated therein for suitably driving the optical system of the camera head 5005 to adjust the magnification and the focal distance.

It is to be noted that, in order to establish compatibility with, for example, a stereoscopic vision (three dimensional (3D) display) or the like, a plurality of imaging elements may be provided on the camera head 5005. In this case, a plurality of relay optical systems is provided in the inside of the lens barrel 5003 in order to guide observation light to each of the plurality of imaging elements.

(Various Apparatus Incorporated in Cart)

The CCU 5039 includes a central processing unit (CPU), a graphics processing unit (GPU) or the like and integrally controls operation of the endoscope 5001 and the display apparatus 5041. In particular, the CCU 5039 performs, for an image signal received from the camera head 5005, various image processes for displaying an image based on the image signal such as, for example, a development process (demosaic process). The CCU 5039 provides the image signal for which the image processes have been performed to the display apparatus 5041. Further, the CCU 5039 transmits a control signal to the camera head 5005 to control driving of the camera head 5005. The control signal may include information relating to an imaging condition such as a magnification or a focal distance.

The display apparatus 5041 displays an image based on an image signal for which the image processes have been performed by the CCU 5039 under the control of the CCU 5039. If the endoscope 5001 is, for example, ready for imaging of a high resolution such as 4K (horizontal pixel number 3840×vertical pixel number 2160), 8K (horizontal pixel number 7680×vertical pixel number 4320) or the like and/or ready for 3D display, then a display apparatus by which corresponding display of the high resolution and/or 3D display are possible may be used as the display apparatus 5041. Where the apparatus is ready for imaging of a high resolution such as 4K or 8K, if the display apparatus used as the display apparatus 5041 has a size of not less than 55 inches, then a more immersive experience can be obtained.

Further, depending on the application, a plurality of display apparatus 5041 having different resolutions and/or different sizes may also be provided.

The light source apparatus 5043 includes a light source such as, for example, a light emitting diode (LED) and supplies irradiation light for imaging of a surgical region to the endoscope 5001.

The arm control apparatus 5045 includes a processor such as a CPU, for example, and operates in accordance with a certain program to control driving of the arm unit 5031 of the support arm apparatus 5027 in accordance with a certain controlling method.

An input apparatus 5047 is an input interface for the endoscopic surgery system 5000. A user can perform inputting of various kinds of information or instruction inputting to the endoscopic surgery system 5000 through the input apparatus 5047. For example, the user would input various kinds of information relating to surgery such as physical information of a patient, information regarding a surgical procedure of the surgery and so forth through the input apparatus 5047. Further, the user would input, for example, an instruction to drive the arm unit 5031, an instruction to change an imaging condition (type of irradiation light, magnification, focal distance or the like) by the endoscope 5001, an instruction to drive the energy device 5021 or the like through the input apparatus 5047.

The type of the input apparatus 5047 is not limited and the input apparatus 5047 may be that of any one of various known input apparatus. As the input apparatus 5047, for example, a mouse, a keyboard, a touch panel, a switch, a foot switch 5057 and/or a lever or the like may be applied. Where a touch panel is used as the input apparatus 5047, it may be provided on the display face of the display apparatus 5041.

Otherwise, the input apparatus 5047 is a device to be mounted on a user such as, for example, a glasses type wearable device or a head mounted display (HMD), and various kinds of inputting are performed in response to a gesture or a line of sight of the user detected by any of the devices mentioned. Further, the input apparatus 5047 includes a camera which can detect a motion of a user, and various kinds of inputting are performed in response to a gesture or a line of sight of a user detected from a video imaged by the camera. Further, the input apparatus 5047 includes a microphone which can collect the voice of a user, and various kinds of inputting are performed by voice collected by the microphone. By configuring the input apparatus 5047 such that various kinds of information can be inputted in a contactless fashion in this manner, especially a user who belongs to a clean area (for example, the surgeon 5067) can operate an apparatus belonging to an unclean area in a contactless fashion. Further, since the user can operate an apparatus without releasing a possessed surgical tool from its hand, user convenience is improved.

A treatment tool control apparatus 5049 controls driving of the energy device 5021 for cautery or incision of a tissue, sealing of a blood vessel or the like. A pneumoperitoneum apparatus 5051 feeds gas into a body cavity of the patient 5071 through the pneumoperitoneum tube 5019 to inflate the body cavity in order to secure the field of view of the endoscope 5001 and secure the working space for the surgeon. A recorder 5053 is an apparatus capable of recording various kinds of information relating to surgery. A printer 5055 is an apparatus capable of printing various kinds of information relating to surgery in various forms such as a text, an image or a graph.

In the following, especially a characteristic configuration of the endoscopic surgery system 5000 is described in more detail.

(Support Arm Apparatus)

The support arm apparatus 5027 includes the base unit 5029 serving as a base, and the arm unit 5031 extending from the base unit 5029. In the example illustrated, the arm unit 5031 includes the plurality of joint units 5033a, 5033b and 5033c and the plurality of links 5035a and 5035b connected to each other by the joint unit 5033b. In FIG. 1, for simplified illustration, the configuration of the arm unit 5031 is illustrated in a simplified form. Actually, the shape, number and arrangement of the joint units 5033a to 5033c and the links 5035a and 5035b and the direction and so forth of axes of rotation of the joint units 5033a to 5033c can be set suitably such that the arm unit 5031 has a desired degree of freedom. For example, the arm unit 5031 may preferably be configured such that it has a degree of freedom not less than 6 degrees of freedom. This makes it possible to move the endoscope 5001 freely within the movable range of the arm unit 5031. Consequently, it becomes possible to insert the lens barrel 5003 of the endoscope 5001 from a desired direction into a body cavity of the patient 5071.

An actuator is provided in each of the joint units 5033a to 5033c, and the joint units 5033a to 5033c are configured to be rotatable about a certain axis of rotation in accordance with the driving of the respective actuators. The driving of the actuators is controlled by the arm control apparatus 5045 to control the rotational angle of each of the joint units 5033a to 5033c thereby to control driving of the arm unit 5031. Consequently, control of the position and the posture of the endoscope 5001 can be implemented. At this point, the arm control apparatus 5045 can control driving of the arm unit 5031 by various known controlling methods such as force control or position control.

For example, if the surgeon 5067 suitably performs operation inputting through the input apparatus 5047 (including the foot switch 5057), then driving of the arm unit 5031 may be controlled suitably by the arm control apparatus 5045 in response to the operation input to control the position and the posture of the endoscope 5001. After the endoscope 5001 at the distal end of the arm unit 5031 is moved from an arbitrary position to a different arbitrary position by the control just described, the endoscope 5001 can be supported fixedly at the position after the movement. It is to be noted that the arm unit 5031 may be operated in a master-slave fashion. In this case, the arm unit 5031 may be remotely controlled by the user through the input apparatus 5047 which is placed at a place remote from the operating room.

Further, in a case where force control is applied, the arm control apparatus 5045 may perform so-called power-assisted control to drive the actuators of the joint units 5033a to 5033c such that the arm unit 5031 may receive external force by the user and move smoothly following the external force. With this arrangement, when the user moves the arm unit 5031 while touching the arm unit 5031 directly, the arm unit 5031 can be moved with comparatively weak force. Accordingly, it becomes possible for the user to move the endoscope 5001 more intuitively with a simpler and easier operation, and user convenience can be improved.

Here, generally in endoscopic surgery, the endoscope 5001 is supported by a medical doctor called scopist. In contrast, where the support arm apparatus 5027 is used, the position of the endoscope 5001 can be fixed more certainly without hands, and therefore, an image of a surgical region can be obtained stably and surgery can be performed smoothly.

It is to be noted that the arm control apparatus 5045 may not necessarily be provided on the cart 5037. Further, the arm control apparatus 5045 may not necessarily be a single apparatus. For example, the arm control apparatus 5045 may be provided in each of the joint units 5033a to 5033c of the arm unit 5031 of the support arm apparatus 5027 such that the multiple of arm control apparatus 5045 cooperate with each other to implement driving control of the arm unit 5031.

(Light Source Apparatus)

The light source apparatus 5043 supplies irradiation light upon imaging of a surgical region to the endoscope 5001. The light source apparatus 5043 includes a white light source which includes, for example, an LED, a laser light source or a combination of them. In this case, where a white light source includes a combination of red, green, and blue (RGB) laser light sources, since the output intensity and the output timing can be controlled with a high degree of accuracy for each color (each wavelength), adjustment of the white balance of a picked up image can be performed by the light source apparatus 5043. Further, in this case, if laser beams from the respective RGB laser light sources are irradiated time-divisionally on an observation target and driving of the imaging elements of the camera head 5005 is controlled in synchronism with the irradiation timings, then images individually corresponding to the R, G and B colors can be picked up time-divisionally. According to the method just described, a color image can be obtained even if a color filter is not provided for the imaging element.

Further, driving of the light source apparatus 5043 may be controlled such that the intensity of light to be outputted is changed for each predetermined time. By controlling driving of the imaging element of the camera head 5005 in synchronism with the timing of the change of the intensity of light to acquire images time-divisionally and synthesizing the images, an image of a high dynamic range free from underexposed blocked up shadows and overexposed highlights can be created.

Further, the light source apparatus 5043 may be configured to supply light of a predetermined wavelength band ready for special light observation. In special light observation, for example, by utilizing the wavelength dependency of absorption of light in a body tissue to irradiate light of a narrower wavelength band in comparison with irradiation light upon ordinary observation (namely, white light), so-called narrow band light observation (narrow band imaging) of imaging a predetermined tissue such as a blood vessel of a superficial portion of the mucous membrane or the like in a high contrast is performed. Alternatively, in special light observation, fluorescent observation for obtaining an image from fluorescent light generated by irradiation of excitation light may be performed. In fluorescent observation, it is possible to perform observation of fluorescent light from a body tissue by irradiating excitation light on the body tissue (autofluorescence observation), to obtain a fluorescent light image by locally injecting a reagent such as indocyanine green (ICG) into a body tissue and irradiating excitation light corresponding to a fluorescent light wavelength of the reagent upon the body tissue, or the like. The light source apparatus 5043 can be configured to supply such narrow-band light and/or excitation light suitable for special light observation as described above.

(Camera Head and CCU)

Figure 2:
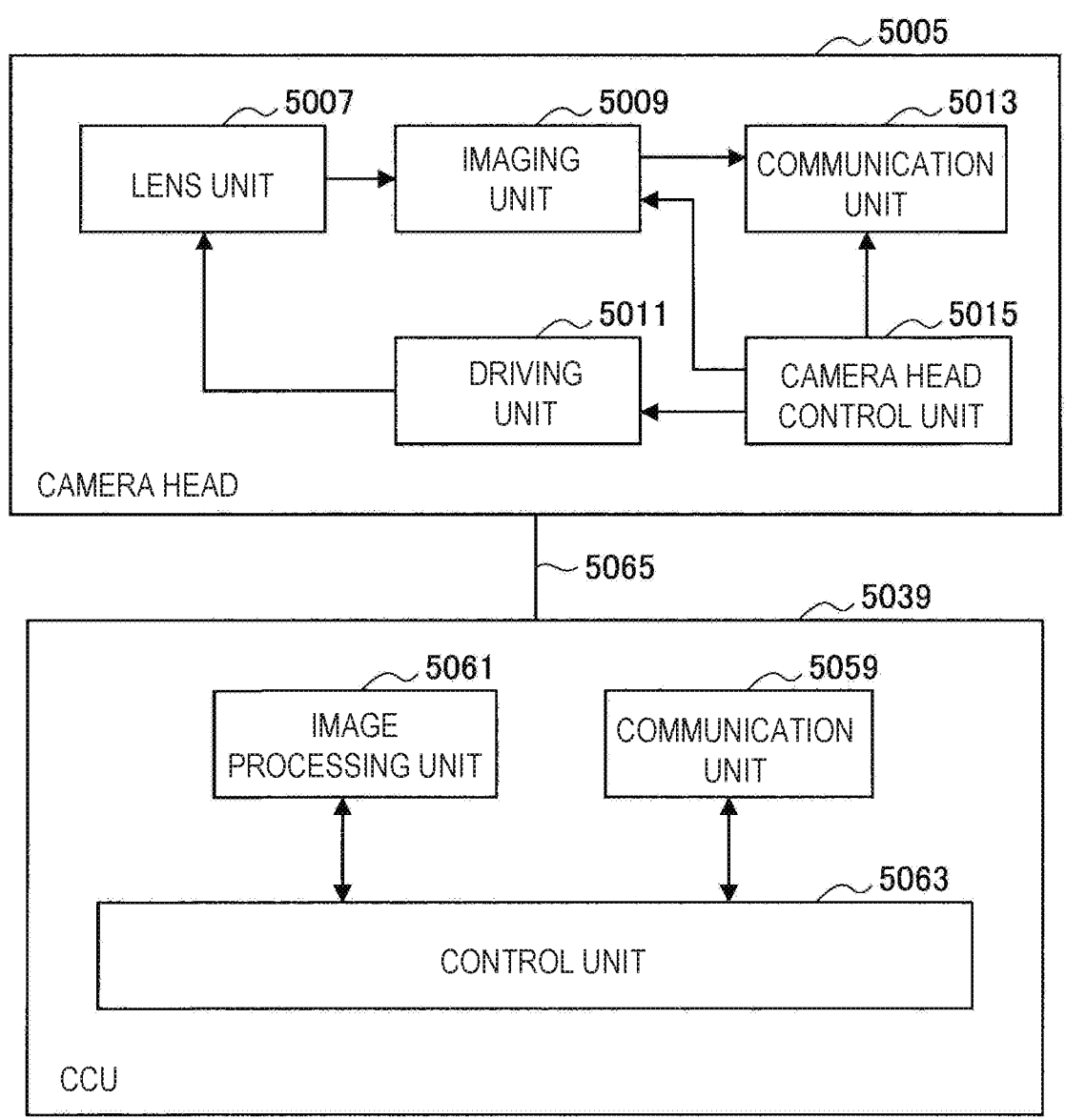
FIG. 2 is a block diagram illustrating an example of a functional configuration of a camera head and a CCU illustrated in FIG. 1.

Functions of the camera head 5005 of the endoscope 5001 and the CCU 5039 are described in more detail with reference to FIG. 2. FIG. 2 is a block diagram illustrating an example of a functional configuration of the camera head 5005 and the CCU 5039 illustrated in FIG. 1.

Referring to FIG. 2, the camera head 5005 has, as functions thereof, a lens unit 5007, an imaging unit 5009, a driving unit 5011, a communication unit 5013 and a camera head control unit 5015. Further, the CCU 5039 has, as functions thereof, a communication unit 5059, an image processing unit 5061 and a control unit 5063. The camera head 5005 and the CCU 5039 are connected to be bidirectionally communicable to each other by a transmission cable 5065.

First, a functional configuration of the camera head 5005 is described. The lens unit 5007 is an optical system provided at a connecting location of the camera head 5005 to the lens barrel 5003. Observation light taken in from a distal end of the lens barrel 5003 is introduced into the camera head 5005 and enters the lens unit 5007. The lens unit 5007 includes a combination of a plurality of lenses including a zoom lens and a focusing lens. The lens unit 5007 has optical properties adjusted such that the observation light is condensed on a light receiving face of the imaging element of the imaging unit 5009. Further, the zoom lens and the focusing lens are configured such that the positions thereof on their optical axis are movable for adjustment of the magnification and the focal point of a picked up image.

The imaging unit 5009 includes an imaging element and disposed at a succeeding stage to the lens unit 5007. Observation light having passed through the lens unit 5007 is condensed on the light receiving face of the imaging element, and an image signal corresponding to the observation image is generated by photoelectric conversion of the imaging element. The image signal generated by the imaging unit 5009 is provided to the communication unit 5013.

As the imaging element which is included by the imaging unit 5009, an image sensor, for example, of the complementary metal oxide semiconductor (CMOS) type is used which has a Bayer array and is capable of picking up an image in color. It is to be noted that, as the imaging element, an imaging element may be used which is ready, for example, for imaging of an image of a high resolution not less than 4K. If an image of a surgical region is obtained in a high resolution, then the surgeon 5067 can comprehend a state of the surgical region in enhanced details and can proceed with the surgery more smoothly.

Further, the imaging element which is included by the imaging unit 5009 is configured such that it has a pair of imaging elements for acquiring image signals for the right eye and the left eye compatible with 3D display. Where 3D display is applied, the surgeon 5067 can comprehend the depth of a living body tissue in the surgical region more accurately. It is to be noted that, if the imaging unit 5009 is configured as that of the multi-plate type, then a plurality of systems of lens units 5007 is provided corresponding to the individual imaging elements of the imaging unit 5009.

Further, the imaging unit 5009 may not necessarily be provided on the camera head 5005. For example, the imaging unit 5009 may be provided just behind the objective lens in the inside of the lens barrel 5003.

The driving unit 5011 includes an actuator and moves the zoom lens and the focusing lens of the lens unit 5007 by a predetermined distance along the optical axis under the control of the camera head control unit 5015. Consequently, the magnification and the focal point of a picked up image by the imaging unit 5009 can be adjusted suitably.

The communication unit 5013 includes a communication apparatus for transmitting and receiving various kinds of information to and from the CCU 5039. The communication unit 5013 transmits an image signal acquired from the imaging unit 5009 as RAW data to the CCU 5039 through the transmission cable 5065. At this point, in order to display a picked up image of a surgical region in low latency, preferably the image signal is transmitted by optical communication. This is because, upon surgery, the surgeon 5067 performs surgery while observing the state of an affected area through a picked up image, it is demanded for a moving image of the surgical region to be displayed on the real time basis as far as possible in order to achieve surgery with a higher degree of safety and certainty. Where optical communication is applied, a photoelectric conversion module for converting an electric signal into an optical signal is provided in the communication unit 5013. After the image signal is converted into an optical signal by the photoelectric conversion module, it is transmitted to the CCU 5039 through the transmission cable 5065.

Further, the communication unit 5013 receives a control signal for controlling driving of the camera head 5005 from the CCU 5039. The control signal includes information relating to imaging conditions such as, for example, information that a frame rate of a picked up image is designated, information that an exposure value upon image picking up is designated and/or information that a magnification and a focal point of a picked up image are designated. The communication unit 5013 provides the received control signal to the camera head control unit 5015. It is to be noted that also the control signal from the CCU 5039 may be transmitted by optical communication. In this case, a photoelectric conversion module for converting an optical signal into an electric signal is provided in the communication unit 5013. After the control signal is converted into an electric signal by the photoelectric conversion module, it is provided to the camera head control unit 5015.

It is to be noted that the imaging conditions such as the frame rate, exposure value, magnification or focal point are set automatically by the control unit 5063 of the CCU 5039 on the basis of an acquired image signal. In other words, a so-called auto exposure (AE) function, an auto focus (AF) function and an auto white balance (AWB) function are incorporated in the endoscope 5001.

The camera head control unit 5015 controls driving of the camera head 5005 on the basis of a control signal from the CCU 5039 received through the communication unit 5013. For example, the camera head control unit 5015 controls driving of the imaging element of the imaging unit 5009 on the basis of information that a frame rate of a picked up image is designated and/or information that an exposure value upon image picking up is designated. Further, for example, the camera head control unit 5015 controls the driving unit 5011 to suitably move the zoom lens and the focus lens of the lens unit 5007 on the basis of information that a magnification and a focal point of a picked up image are designated. The camera head control unit 5015 may further include a function for storing information for identifying the lens barrel 5003 and/or the camera head 5005.

It is to be noted that, by disposing the components such as the lens unit 5007 and the imaging unit 5009 in a sealed structure having high airtightness and waterproofness, the camera head 5005 can be provided with resistance to an autoclave sterilization process.

Now, a functional configuration of the CCU 5039 is described. The communication unit 5059 includes a communication apparatus for transmitting and receiving various kinds of information to and from the camera head 5005. The communication unit 5059 receives an image signal transmitted thereto from the camera head 5005 through the transmission cable 5065. At this point, the image signal may be transmitted preferably by optical communication as described above. In this case, for the compatibility with optical communication, the communication unit 5059 includes a photoelectric conversion module for converting an optical signal into an electric signal. The communication unit 5059 provides the image signal after conversion into an electric signal to the image processing unit 5061.

Further, the communication unit 5059 transmits, to the camera head 5005, a control signal for controlling driving of the camera head 5005. The control signal may also be transmitted by optical communication.

The image processing unit 5061 performs various image processes for an image signal in the form of RAW data transmitted thereto from the camera head 5005. The image processes include various known signal processes such as, for example, a development process, an image quality improving process (a bandwidth enhancement process, a super-resolution process, a noise reduction (NR) process, an image stabilization process, and/or the like) and/or an enlargement process (electronic zooming process). Further, the image processing unit 5061 performs a detection process for an image signal in order to perform AE, AF and AWB.

The image processing unit 5061 includes a processor such as a CPU or a GPU, and when the processor operates in accordance with a predetermined program, the image processes and the detection process described above can be performed. It is to be noted that, where the image processing unit 5061 includes a plurality of GPUs, the image processing unit 5061 suitably divides information relating to an image signal such that image processes are performed in parallel by the plurality of GPUs.

The control unit 5063 performs various kinds of control relating to image picking up of a surgical region by the endoscope 5001 and display of the picked up image. For example, the control unit 5063 generates a control signal for controlling driving of the camera head 5005. At this point, in a case where imaging conditions are inputted by the user, then the control unit 5063 generates a control signal on the basis of the input by the user. Alternatively, where the endoscope 5001 has an AE function, an AF function and an AWB function incorporated therein, the control unit 5063 suitably calculates an optimum exposure value, focal distance and white balance in response to a result of a detection process by the image processing unit 5061 and generates a control signal.

Further, the control unit 5063 controls the display apparatus 5041 to display an image of a surgical region on the basis of an image signal for which image processes have been performed by the image processing unit 5061. At this point, the control unit 5063 recognizes various objects in the surgical region image using various image recognition technologies. For example, the control unit 5063 can recognize a surgical tool such as forceps, a particular living body region, bleeding, mist when the energy device 5021 is used and so forth by detecting the shape, color and so forth of edges of the objects included in the surgical region image. The control unit 5063 causes, when it controls the display apparatus 5041 to display a surgical region image, various kinds of surgery supporting information to be displayed in an overlapping manner with an image of the surgical region using a result of the recognition. Where surgery supporting information is displayed in an overlapping manner and presented to the surgeon 5067, the surgeon 5067 can proceed the surgery with more safety and certainty.

The transmission cable 5065 which connects the camera head 5005 and the CCU 5039 to each other is an electric signal cable ready for communication of an electric signal, an optical fiber ready for optical communication or a composite cable ready for both of electrical and optical communication.

Here, while, in the example illustrated, communication is performed by wired communication using the transmission cable 5065, the communication between the camera head 5005 and the CCU 5039 may be performed otherwise by wireless communication. Where the communication between the camera head 5005 and the CCU 5039 is performed by wireless communication, there is no necessity to lay the transmission cable 5065 in the operating room. Therefore, such a situation that movement of medical staff in the operating room is disturbed by the transmission cable 5065 can be eliminated.

The configuration example of the endoscopic surgery system 5000 to which the technology according to the present disclosure can be applied has been described above.

2. Outline

Subsequently, outline of the technology according to the present disclosure will be described. In medical practice, an endoscope is sometimes used. Here, a case where imaging is performed using an endoscope will be described in more detail.

Figure 3:
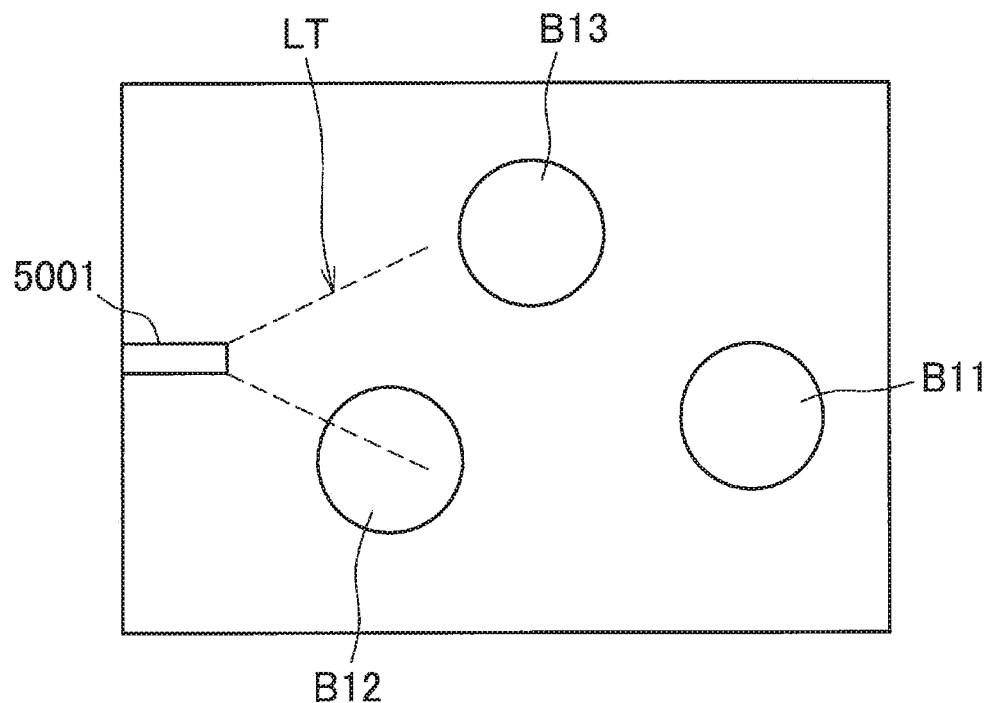
FIG. 3 is a view schematically illustrating an imaging environment in a case where an endoscope is used.
Figure 4:
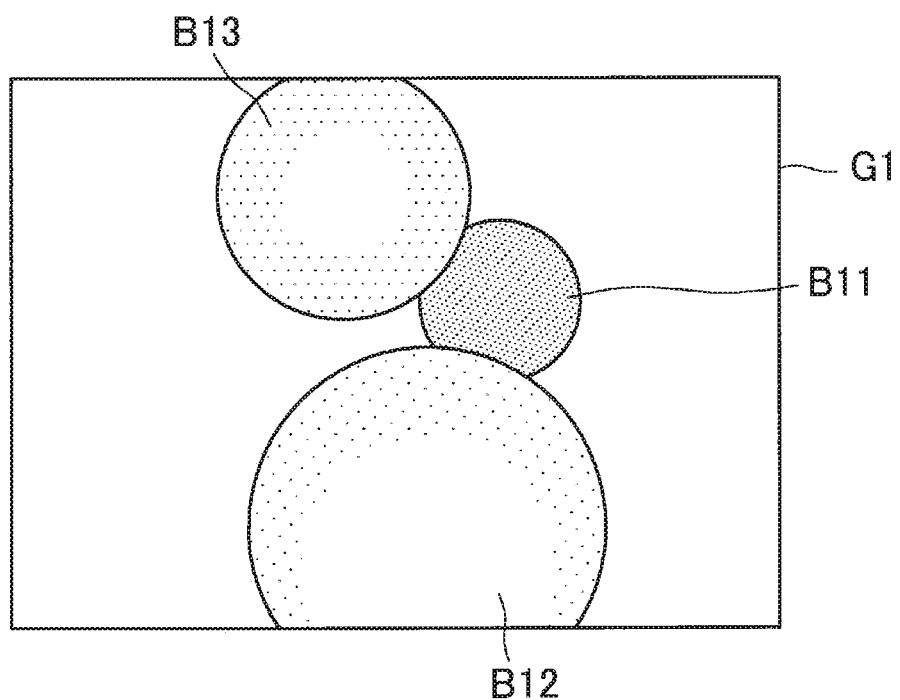
FIG. 4 is a view illustrating an example of an image captured with the endoscope.

FIG. 3 is a view schematically illustrating an imaging environment in a case where the endoscope 5001 is used. FIG. 4 is a view illustrating an example of an image captured with the endoscope 5001. Referring to FIG. 3, the endoscope 5001 and subjects B11 to B13 are illustrated. The subjects B11 to B13 exist in a short distance from the endoscope 5001, and the subjects B11 to B13 have depths. From the endoscope 5001, light LT is radiated on the subjects B11 to B13. The subjects B11 to B13 irradiated with the light LT are imaged by the endoscope 5001.

In this manner, in a case where imaging is performed with the endoscope 5001, generally, the subject exists in a short distance from the endoscope 5001, and the subject has a depth. Therefore, an image captured with the endoscope 5001 (hereinafter, also referred to as an "endoscope image") has characteristics that halation is likely to occur on a front side of the subject and characteristics that blocked-up shadow is likely to occur on a back side of the subject and at a portion of shadow on the subject. In the endoscope image G1 illustrated in FIG. 4, halation occurs on front sides of the subject B12 and the subject B13, and blocked-up shadow occurs on back sides of the subject B12 and the subject B13.

Such a phenomenon can occur in a similar manner also in a case where various medical apparatuses are used in medical practice such as in a case where a microscope is used, as well as in a case where the endoscope 5001 is used. As a method for reducing such halation and blocked-up shadow, there is a technology of acquiring a high dynamic range (HDR) image, in which information of a wide brightness range from a dark portion to a bright portion is acquired.

However, a monitor which displays an image is generally a monitor which can express a brightness range narrower than a brightness range of the HDR image which is acquired as described above. In the following description, a brightness range narrower than the brightness range of the HDR image will be also referred to as a "standard dynamic range (SDR)". Typically, instead of the HDR image itself being output to an SDR monitor, after gradation of the HDR image acquired as described above is compressed and converted into an SDR image, the SDR image is output to the SDR monitor. However, in such a case, it is not possible to sufficiently utilize abundant brightness information of the HDR image.

Figure 5:
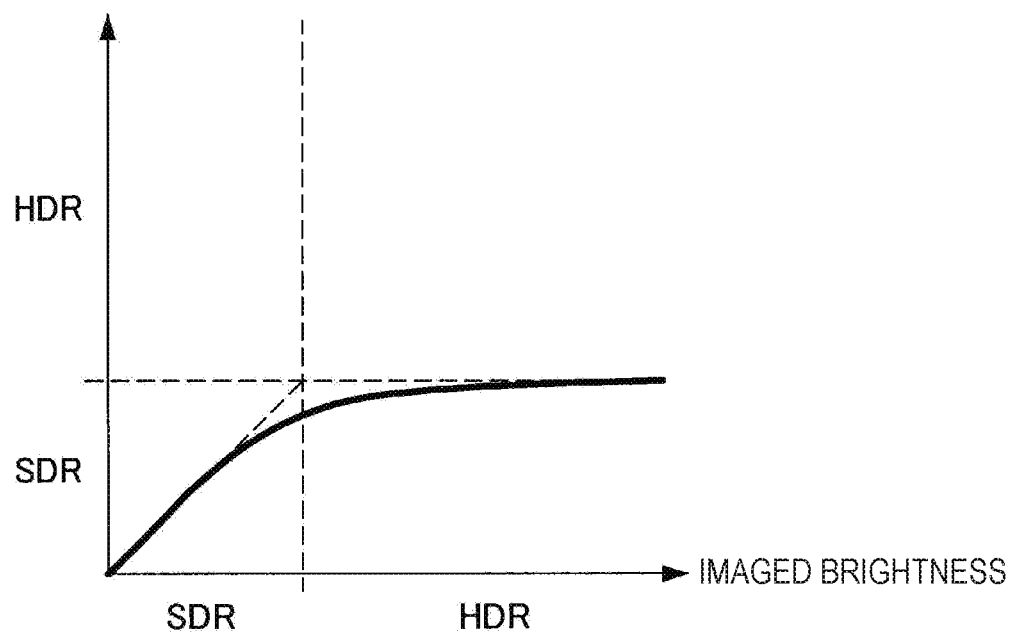
FIG. 5 is a view illustrating an example of an SDR image obtained after gradation compression is performed for an HDR image.

FIG. 5 is a view illustrating an example of the SDR image obtained after gradation compression is performed for the HDR image. FIG. 5 indicates brightness of the endoscope image captured with the endoscope on a horizontal axis as "imaged brightness". Further, FIG. 5 indicates brightness of display of the endoscope image on a vertical axis as "displayed brightness". In the example illustrated in FIG. 5, as a result of gradation compression being performed on a high-brightness side of the endoscope image, a brightness range of display of the endoscope image falls within the SDR.

Meanwhile, in recent years, an HDR monitor which can display information in a wide brightness range from a dark portion to a bright portion has been developed. Therefore, by outputting an HDR image to an HDR monitor with brightness as is without gradation compression being performed for the HDR image acquired as described above, it is possible to sufficiently utilize abundant brightness information of the HDR image.

Figure 6:
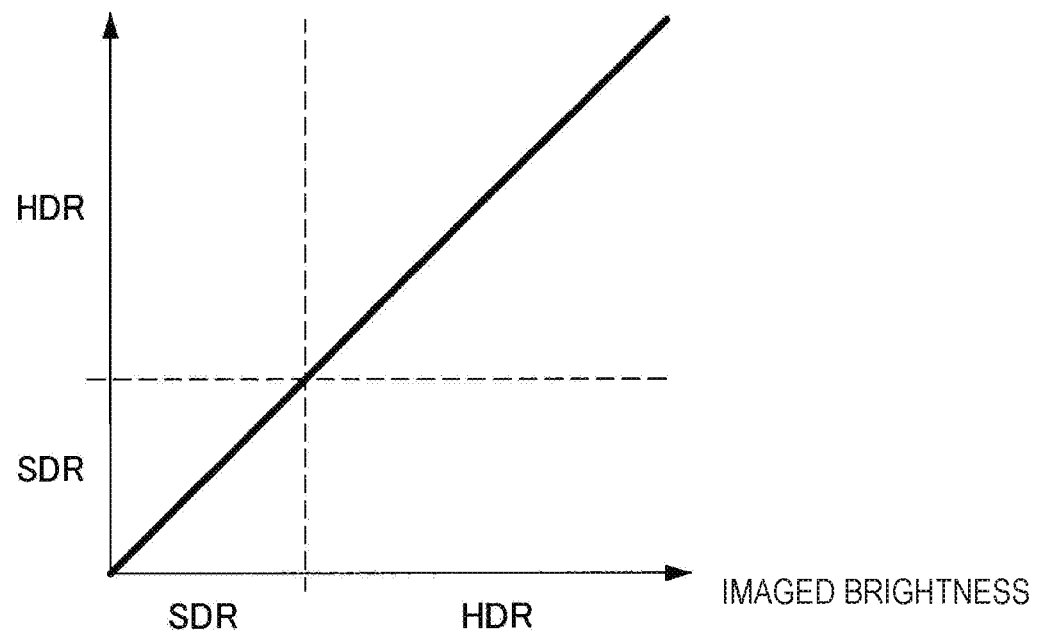
FIG. 6 is a view illustrating an example of an HDR image itself output without gradation compression being performed for the HDR image.

FIG. 6 is a view illustrating an example of the HDR image itself output without gradation compression being performed for the HDR image. In a similar manner to FIG. 5, FIG. 6 indicates brightness of the endoscope image captured with the endoscope on a horizontal axis as "imaged brightness". Further, in a similar manner to FIG. 5, FIG. 6 indicates brightness of display of the endoscope image on a vertical axis as "displayed brightness". In the example illustrated in FIG. 6, because gradation compression is not performed for the endoscope image, a brightness range of display of the endoscope image becomes the HDR.

However, on the other hand, in a case where an HDR image acquired with an endoscope is displayed at an HDR monitor with brightness as is, there is a case where a user feels glare for a portion on a front side intensely illuminated with illumination light, a portion which is extremely bright by specular reflection among the displayed HDR image, and the like. Further, particularly, in diagnosis or surgery using an endoscope, a surgeon gets uncomfortable by continuously watching these HDR images for a long period of time, which may become hindrance of implementation of diagnosis or surgery.

Further, there is a case where, as a result of a bright display portion increasing, visibility of a dark portion relatively decreases. Still further, in a case where a plurality of monitors is connected to the endoscope, and SDR monitors and HDR monitors are mixed among the plurality of monitors, even if a signal output to the HDR monitor so as to conform to the HDR monitor is output to the SDR monitor as is, an appropriate image is not displayed at the SDR monitor.

Therefore, in the present specification, a technology of adaptively converting an HDR image into an appropriate output image and outputting the image to the HDR monitor will be mainly proposed. More specifically, in the present specification, a technology will be proposed which is capable of reducing glare to be felt by the user for an output image by the HDR monitor in a case where the image is caused to be displayed at the HDR monitor on the basis of the HDR image.

In addition, in the present specification, a technology will be proposed which improves user's visibility of a portion from a dark portion to a bright portion of the output image by the HDR monitor. Further, in the present specification, a technology will be proposed which outputs an appropriate output image to a monitor to be connected to the endoscope.

The outline of the technology according to the present disclosure has been described above.

3. Basic Configuration

Figure 7:
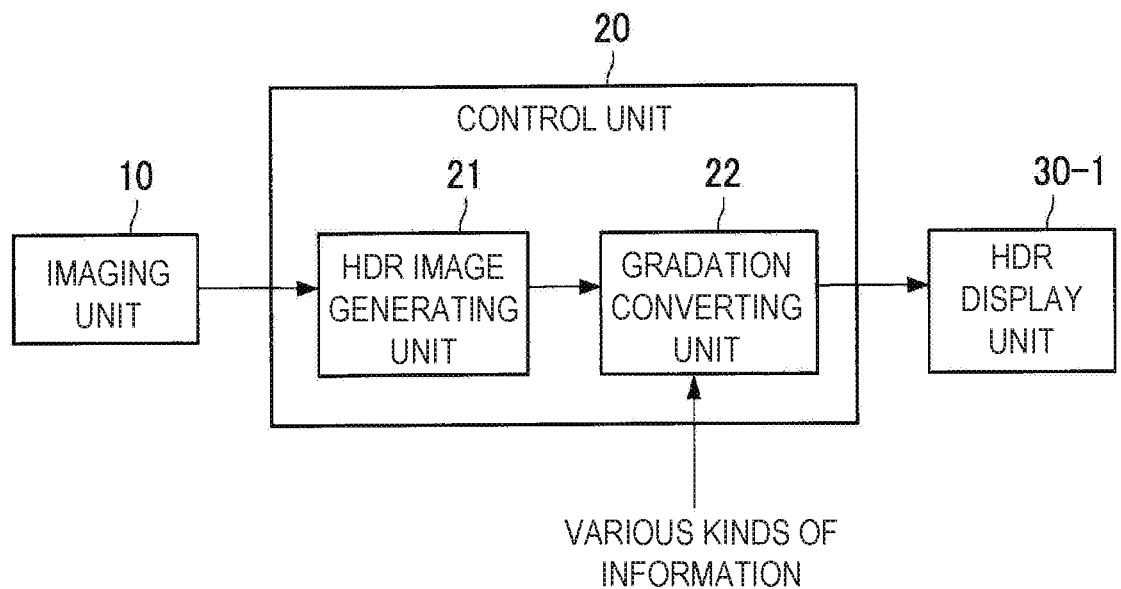
FIG. 7 is a block diagram illustrating a functional configuration example of a control unit provided at the CCU according to an embodiment of the present disclosure.

Subsequently, a configuration example of a control unit provided at a CCU according to the embodiment of the present disclosure will be described. FIG. 7 is a block diagram illustrating a functional configuration example of the control unit provided at the CCU according to the embodiment of the present disclosure. As illustrated in FIG. 7, the control unit 20 provided at the CCU according to the embodiment of the present disclosure includes an HDR image generating unit 21 and a gradation converting unit 22. An imaging unit 10 is connected to the HDR image generating unit 21. An HDR display unit (HDR monitor) 30-1 is connected to the gradation converting unit 22.

The imaging unit 10, which includes an image sensor, images a subject using the image sensor. In more detail, light is radiated on a subject inside a living organism by a light source which is not illustrated, and the imaging unit 10 images the subject coaxially with an optical axis of the light source which is not illustrated. For example, the light source which is not illustrated can correspond to the light source apparatus 5043 illustrated in FIG. 1. Further, the imaging unit 10 acquires brightness of the subject as pixel value information using the image sensor. The imaging unit 10 can correspond to the imaging unit 5009 illustrated in FIG. 2. Note that the image sensor may include a 3CCD imaging element.

The control unit 20 controls the light source which is not illustrated. Further, the control unit 20 controls the imaging unit 10 and the HDR display unit 30-1. Note that the control unit 20 illustrated in FIG. 7 can correspond to the control unit 5063 illustrated in FIG. 2.

The HDR image generating unit 21 generates an HDR image using the pixel value information obtained by the imaging unit 10. Here, the HDR image can be defined in various manners. For example, the HDR image is only required to be a signal compliant with HDR standards. More specifically, the signal compliant with the HDR standards may be a signal supporting hybrid log-gamma (HLG) or may be a signal supporting perceptual quantization (PQ).

Alternatively, if a brightness range of the image is equal to or higher than predetermined brightness, the image can be regarded as the HDR image. Here, the predetermined brightness may be specifically any value. As an example, if the brightness range of the image is equal to or greater than 1000 [$cd/m^2$], the image can be regarded as the HDR image.

A monitor which displays an image is generally a monitor which can express a brightness range narrower than a brightness range of the HDR image which is acquired as described above. In the following description, a brightness range narrower than the brightness range of the HDR image will be also referred to as a "standard dynamic range (SDR)". Typically, instead of the HDR image itself being output to an SDR monitor, after gradation of the HDR image acquired as described above is compressed and converted into an SDR image, the SDR image is output to the SDR monitor. However, in such a case, it is not possible to sufficiently utilize abundant brightness information of the HDR image.

FIG. 5 is a view illustrating an example of the SDR image obtained after gradation compression is performed for the HDR image. FIG. 5 indicates brightness of the endoscope image captured with the endoscope on a horizontal axis as "imaged brightness". Further, FIG. 5 indicates brightness of display of the endoscope image on a vertical axis as "displayed brightness". In the example illustrated in FIG. 5, as a result of gradation compression being performed on a high-brightness side of the endoscope image, a brightness range of display of the endoscope image falls within the SDR.

A method for generating an HDR image is not particularly limited. For example, as the method for generating an HDR image, it is also possible to employ a method in which a bright image and a dark image are acquired by exposure being alternately changed with time, and the images are synthesized, or a method in which a bright pixel and a dark pixel with different exposure are disposed on the image sensor, and the pixels are synthesized.

Note that, in the embodiment of the present disclosure, a case will be mainly described where the HDR image generating unit 21 generates an HDR image using the pixel value information obtained by the image sensor. However, in a case where the image sensor can acquire an HDR image (wide brightness information from a dark portion to a bright portion) from the beginning, the HDR image generating unit 21 is not required, and the pixel value information obtained by the image sensor may be used as is by the gradation converting unit 22.

The gradation converting unit 22 adjusts gradation for the HDR image (first image signal) obtained by the HDR image generating unit 21. As a result of gradation being adjusted by the gradation converting unit 22, the HDR image obtained by the HDR image generating unit 21 is converted into an output image. The output image is also an image compliant with the HDR standards (HDR image). The gradation converting unit 22 performs control so that the output image compliant with the HDR standards is displayed at the HDR display unit 30-1 by outputting the output image compliant with the HDR standards to the HDR display unit 30-1.

According to such a configuration, in a case where an image is caused to be displayed at the HDR display unit 30-1 on the basis of the HDR image, the HDR image after gradation is adjusted is output to the HDR display unit 30-1. Therefore, it is possible to reduce glare to be felt by the user for the output image by the HDR display unit 30-1.

For example, as illustrated in FIG. 7, the gradation converting unit 22 adjusts gradation for the HDR image (first image signal) obtained by the HDR image generating unit 21 on the basis of various kinds of information. Here, the various kinds of information will be specifically described in respective embodiments which will be described below.

The HDR display unit 30-1 includes a display at which an HDR image can be displayed (that is, the HDR display unit 30-1 includes a display compliant with the HDR standards). The HDR display unit 30-1 outputs (displays) an HDR image (output image) after gradation is adjusted by the gradation converting unit 22.

A configuration example of the control unit provided at the CCU according to the embodiment of the present disclosure has been described above.

4. Respective Embodiments

Respective embodiments assuming the configuration example of the control unit described in the above "3. Basic Configuration" will be described below.

4-1. First Embodiment

A first embodiment of the present disclosure will be described first.

Figure 8:
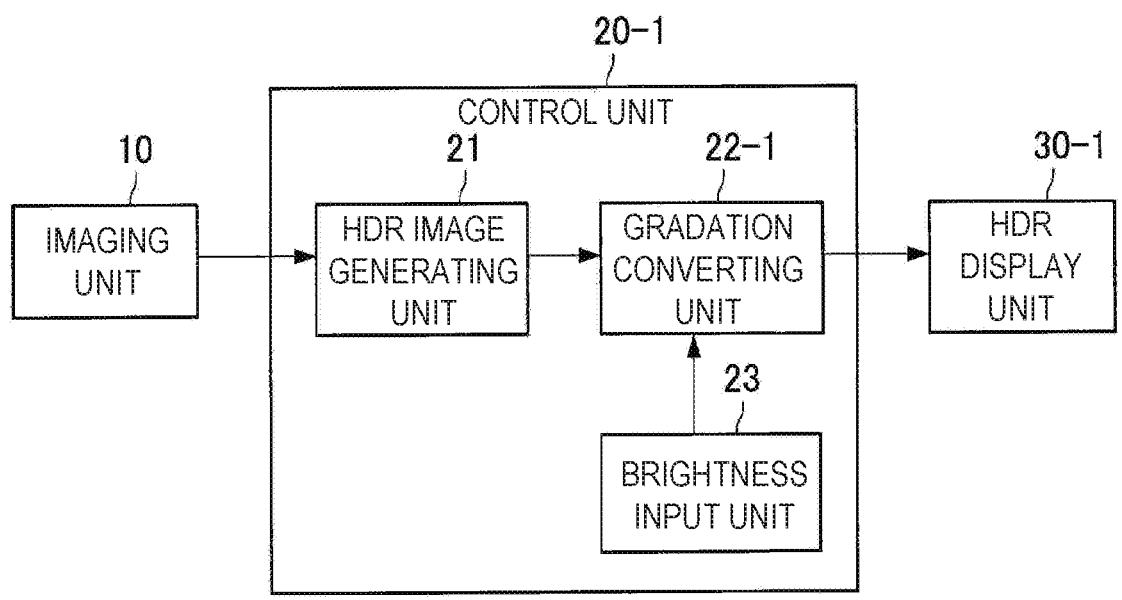
FIG. 8 is a view illustrating a configuration example of a control unit according to a first embodiment of the present disclosure.

FIG. 8 is a view illustrating a configuration example of a control unit 20-1 according to the first embodiment of the present disclosure. As illustrated in FIG. 8, the control unit 20-1 according to the first embodiment of the present disclosure differs from the control unit 20 illustrated in FIG.

7 in that a brightness input unit 23 is provided, and a gradation converting unit 22-1 is provided in place of the gradation converting unit 22. Therefore, in the following description, the brightness input unit 23 and the gradation converting unit 22-1 will be mainly described among the control unit 20-1 according to the first embodiment of the present disclosure, and detailed description of other configurations will be omitted.

Here, in a case where an endoscope image is displayed, unlike with a case where an image for viewing such as a TV program is displayed, there is a case where it is important to display an image which does not make a user get uncomfortable by glare even if the user watches the image for a long period of time, rather than truly express brightness. Therefore, in the first embodiment of the present disclosure, the user is allowed to designate information regarding brightness so as to prevent the user from getting uncomfortable even if the user watches an output image for a long period of time when the output image is caused to be displayed at the HDR display unit 30-1. Here, as an example of the information regarding brightness, a case will be described where a maximum value of brightness (a maximum brightness value of an image signal) can be designated.

The brightness input unit 23 accepts the maximum value of brightness designated by the user. For example, input of the maximum value of brightness designated by the user may be directly accepted by the input apparatus 5047 illustrated in FIG. 1, and the maximum value of brightness whose input is accepted by the input apparatus 5047 may be accepted by the brightness input unit 23. While a case is assumed here where one of three stages ("high", "medium" and "low") is selected as the maximum value of brightness, the maximum value of brightness may be designated from any number of options, or may be directly designated with a numerical value.

The gradation converting unit 22-1 adjusts gradation for the HDR image (first image signal) obtained by the HDR image generating unit 21 on the basis of the maximum value of brightness designated by the user.

Figure 9:
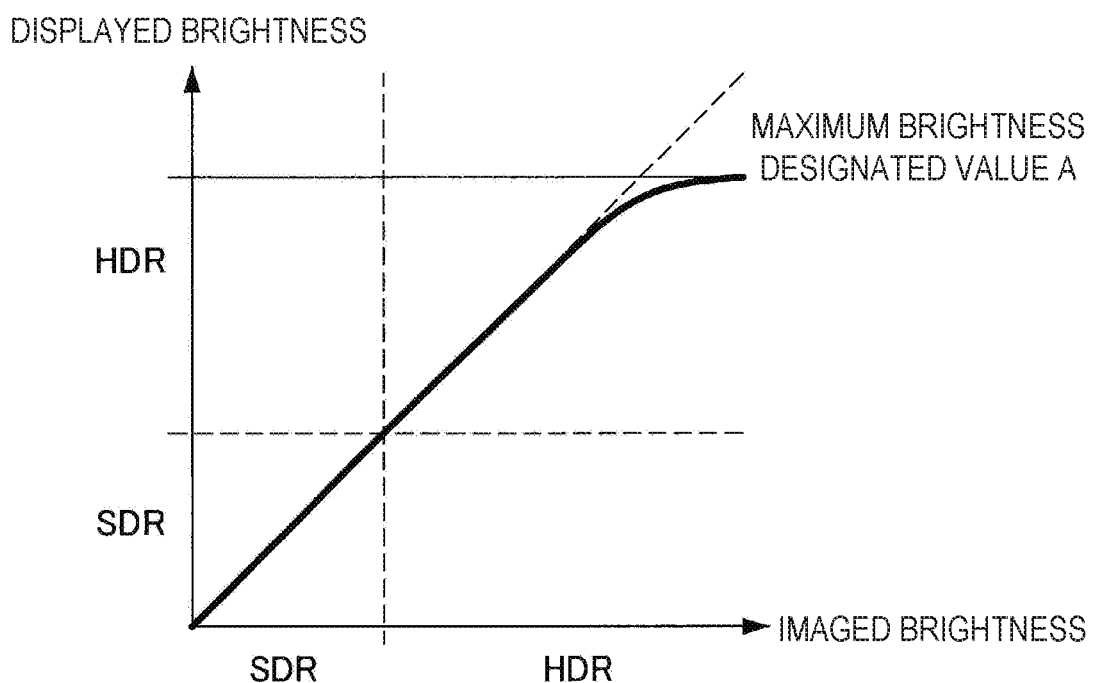
FIG. 9 is a view illustrating an example of an output image in a case where a maximum value of brightness is designated by a user.
Figure 10:
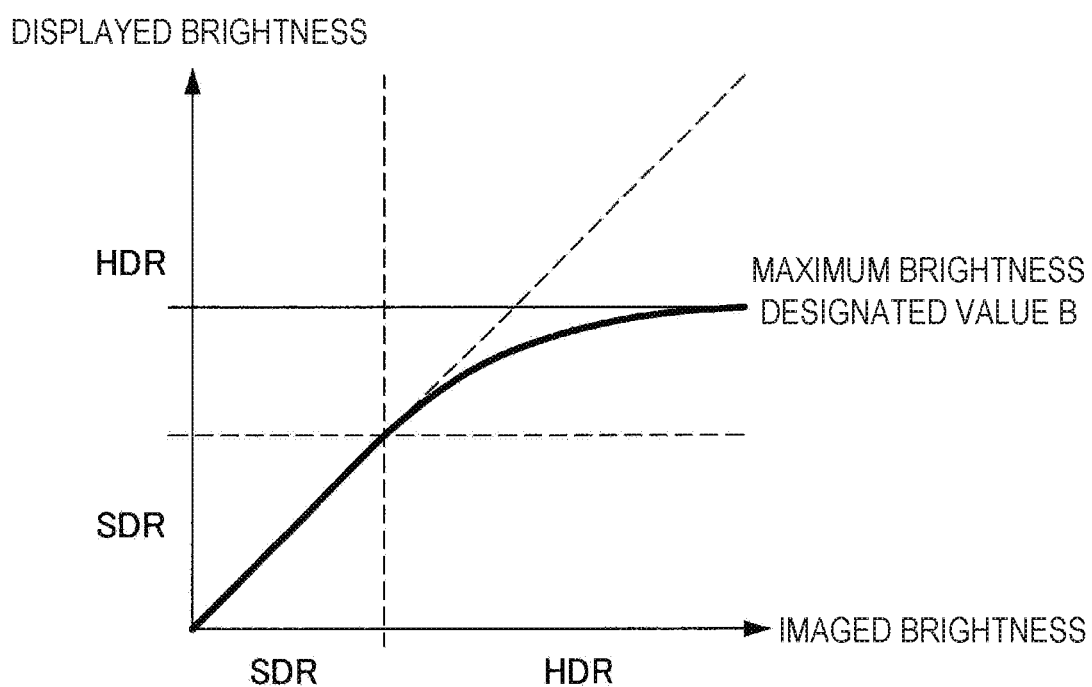
FIG. 10 is a view illustrating an example of an output image in a case where a maximum value of brightness is designated by the user.

FIGS. 9 and 10 are views respectively illustrating examples of the output images in a case where the maximum value of brightness is designated by the user. Referring to FIG. 9, as an example of the maximum value of brightness designated by the user, a "maximum brightness designated value A" (=first brightness value) is presented. The gradation converting unit 22-1 adjusts gradation of the HDR image (first image signal) so that all brightness (brightness values) of the HDR image (first image signal) obtained by the HDR image generating unit 21 becomes equal to or less than this "maximum brightness designated value A". For example, as illustrated in FIG. 9, the gradation converting unit 22-1 compresses gradation of the HDR image (first image signal) so as to be gentle.

Here, the gradation converting unit 22-1 preferably compresses only a bright portion of the HDR image (first image signal) instead of compressing gradation of the whole HDR image (first image signal). That is, the gradation converting unit 22-1 preferably adjusts gradation so that brightness values become equal to or less than the "maximum brightness designated value A" for pixel signals greater than a second brightness value among the HDR image (first image signal), and does not preferably adjust gradation for pixel signals whose brightness values are equal to or less than the second brightness value. With this arrangement, it is possible to reduce only brightness of an extremely bright portion for which the user is to feel glare, without changing how a normal bright portion looks.

Referring to FIG. 10, as an example of the maximum value of brightness designated by the user, a "maximum brightness designated value B" which is smaller than the "maximum brightness designated value A" illustrated in FIG. 9 is presented. Also in such a case, the gradation converting unit 22-1 adjusts gradation of the HDR image so that brightness (brightness values) of the whole HDR image obtained by the HDR image generating unit 21 becomes equal to or less than this "maximum brightness designated value B".

Also in such a case, the gradation converting unit 22-1 preferably compresses only a bright portion of the HDR image instead of compressing gradation of the whole HDR image. That is, the gradation converting unit 22-1 preferably adjusts gradation so that brightness values become equal to or less than the "maximum brightness designated value B" for pixel signals greater than a second brightness value among the HDR image, and does not preferably adjust gradation for pixel signals whose brightness values are equal to or less than the second brightness value.

Note that, here, a case where the user is allowed to designate the maximum value of brightness has been described as an example of the information regarding brightness. However, the information regarding brightness is not limited to the maximum value of brightness.

For example, as an example of the information regarding brightness, it is also possible to allow the user to designate a minimum value of brightness (minimum brightness value of an image signal). In this event, the gradation converting unit 22-1 is only required to adjust gradation for the HDR image (first image signal) obtained by the HDR image generating unit 21 on the basis of the minimum value of brightness designated by the user.

Alternatively, as an example of the information regarding brightness, it is also possible to allow the user to designate an adjustment rate of gradation of the image signal. In this event, the gradation converting unit 22-1 is only required to adjust gradation for the HDR image (first image signal) obtained by the HDR image generating unit 21 on the basis of the adjustment rate of gradation designated by the user.

Further, the gradation converting unit 22-1 may adjust gradation for the HDR image (first image signal) obtained by the HDR image generating unit 21 on the basis of observation mode information designated by the user in place of the information regarding brightness designated by the user. For example, an observation mode may be selectable from a special light observation mode (such as, for example, an infrared light observation mode and a narrow-band light observation mode) and a normal light observation mode.

For example, the gradation converting unit 22-1 may perform gradation compression for the HDR image (first image signal) more intensely in a case where the special light observation mode is designated by the user than in a case where the normal light observation mode is designated by the user. In the above-described examples, gradation compression illustrated in FIG. 10 is more intense than gradation compression illustrated in FIG. 9. Further, the gradation converting unit 22-1 does not have to perform gradation compression for the HDR image (first image signal) in a case where an observation mode is not designated by the user.

The first embodiment of the present disclosure has been described above.

4-2. Second Embodiment

Subsequently, a second embodiment of the present disclosure will be described.

Figure 11:
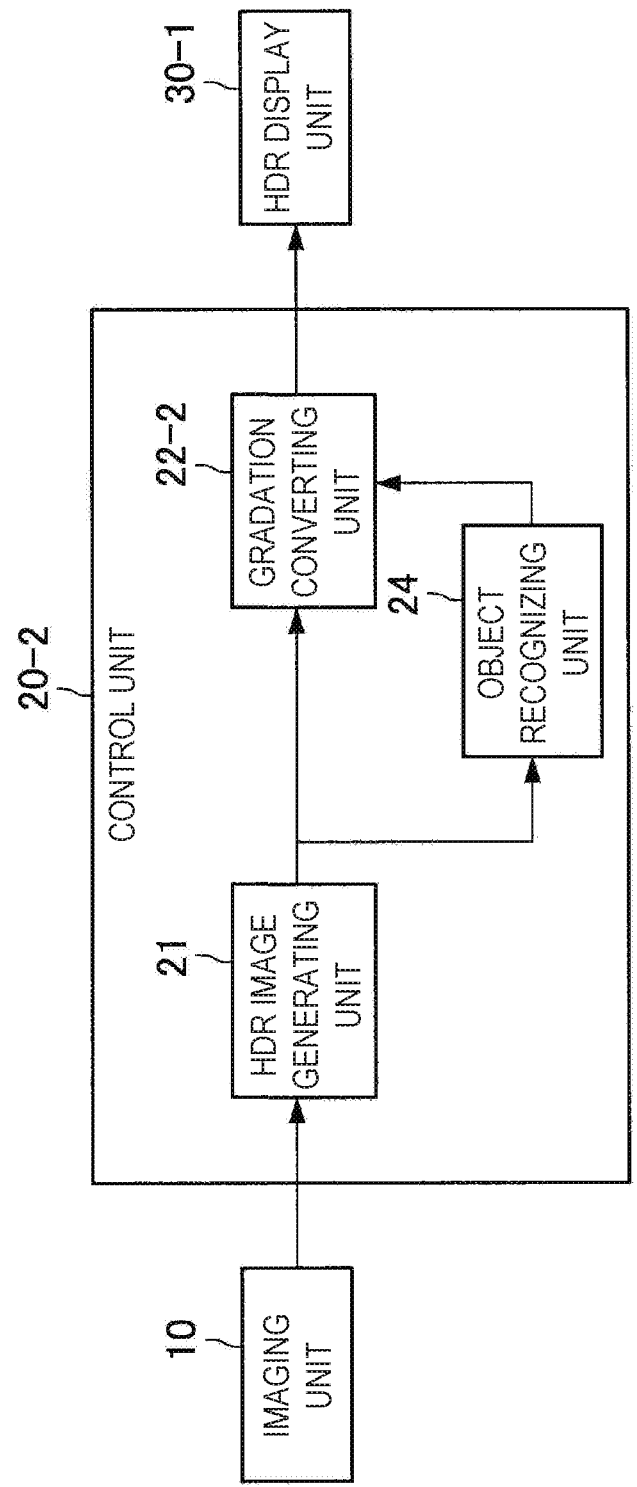
FIG. 11 is a view illustrating a configuration example of a control unit according to a second embodiment of the present disclosure.

FIG. 11 is a view illustrating a configuration example of a control unit 20-2 according to the second embodiment of the present disclosure. As illustrated in FIG. 11, the control unit 20-2 according to the second embodiment of the present disclosure differs from the control unit 20 illustrated in FIG. 7 in that an object recognizing unit 24 is provided, and a gradation converting unit 22-2 is provided in place of the gradation converting unit 22. Therefore, in the following description, the object recognizing unit 24 and the gradation converting unit 22-2 will be mainly described among the control unit 20-2 according to the second embodiment of the present disclosure, and detailed description of other configurations will be omitted.

Here, objects in the endoscope image include an object for which it would be better to truly express brightness and an object for which it is not necessary to truly express brightness. For example, it is desired to truly reproduce brightness of an organ in the body so that the user can correctly recognize a state of the organ. Meanwhile, it is not necessary to truly reproduce brightness of a surgical instrument. Particularly, a metal surgical instrument has high reflectance, which becomes extremely high brightness and leads to eyestrain. Therefore, in the second embodiment, a case will be described where an object in the endoscope image is recognized, and gradation of the HDR image is converted on the basis of the recognition result.

Figure 12:
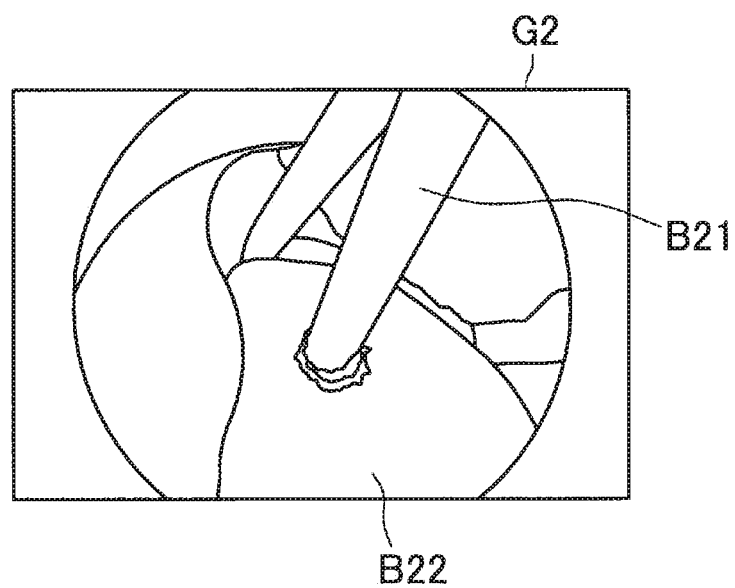
FIG. 12 is a view illustrating an example of an endoscope image including a surgical instrument.

The object recognizing unit 24 performs object recognition for the HDR image (first image signal) obtained by the HDR image generating unit 21. FIG. 12 is a view illustrating an example of the endoscope image including a surgical instrument. Referring to FIG. 12, as an example of a surgical instrument B21, a forceps is in the endoscope image G2. Further, an organ B22 is in the endoscope image G2. The surgical instrument B21 and the organ B22 are recognized by the object recognizing unit 24.

The gradation converting unit 22-2 determines a region (first region) in which gradation is to be adjusted on the basis of a result of the object recognition by the object recognizing unit 24, and performs control so as to adjust gradation of a pixel signal included in the region where gradation is to be adjusted, and so as not to adjust gradation of a pixel signal included in a region other than the region in which gradation is to be adjusted. For example, the gradation converting unit 22-2 specifies a region (second region) including a mask, a surgical tool, gauze, mist or body tissues on the basis of the result of the object recognition by the object recognizing unit 24 and determines a region in which gradation is to be adjusted on the basis of the second region.

Figure 13:
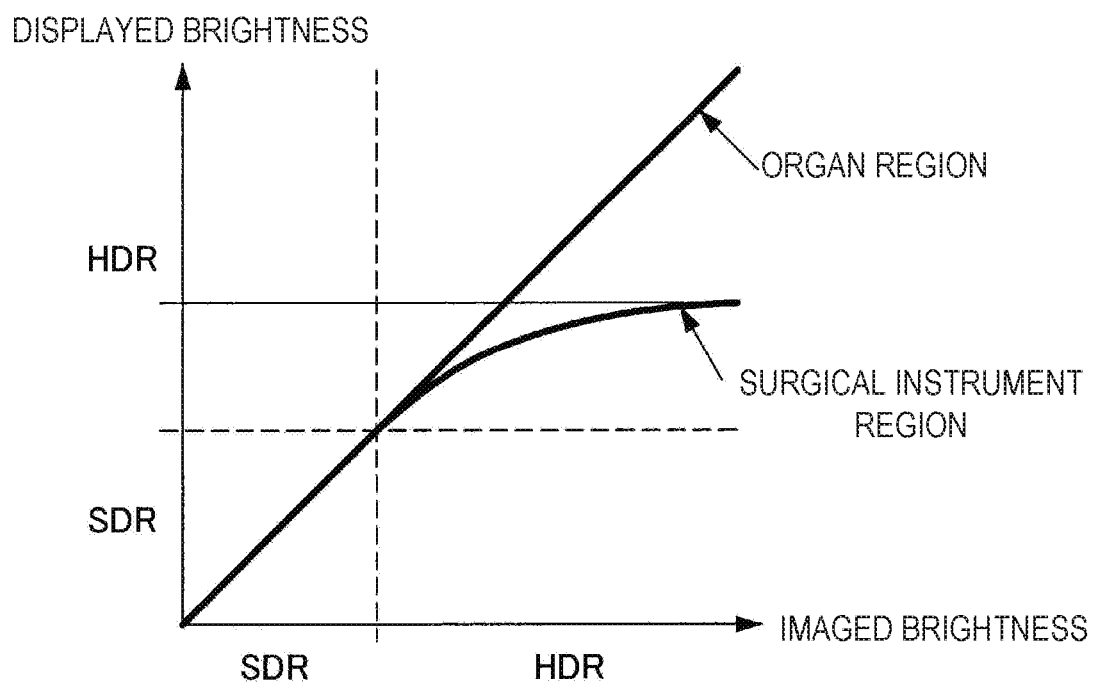
FIG. 13 is a view illustrating examples of output images obtained after gradation compression is performed on the basis of an object recognition result.

FIG. 13 is a view illustrating examples of the output images obtained after gradation compression is performed on the basis of the object recognition result. In the example illustrated in FIG. 12, the surgical instrument B21 and the organ B22 are recognized by the object recognizing unit 24. The gradation converting unit 22-2 may specify a surgical instrument region on the basis of the recognition result of the surgical instrument B21 and may determine the surgical instrument region as a region in which gradation is to be adjusted. Alternatively, the gradation converting unit 22-2 may specify an organ region on the basis of the recognition result of the organ B22 and may determine a region other than the organ region as the region in which gradation is to be adjusted.

Referring to FIG. 13, gradation of the image signal included in the organ region is not compressed, and gradation of the image signal included in the surgical instrument region is compressed. The gradation converting unit 22-2 adjusts gradation of the image signal so that brightness (brightness value) of the image signal included in the surgical instrument region becomes equal to or less than a "maximum brightness limit value". While, in the example illustrated in FIG. 13, the "maximum brightness limit value" is set within the range of the HDR, the maximum brightness limit value may be set within the range of the SDR.

Note that, while an example has been described here where a surgical instrument is recognized as an example of the surgical tool, there can be a case where a mask, gauze, mist, or the like, is recognized. Because it is assumed that a mask, gauze, or the like, is less likely to be bright compared to a metal surgical instrument, it would be better that the image signal included in the region of the mask or the gauze is subjected to gradation compression more weakly than the image signal included in the region of the metal surgical instrument. Meanwhile, because brightness of mist can change in accordance with sizes of particles forming the mist, it would be better that intensity of gradation compression of the image signal included in the region of the mist depends on sizes of particles forming the mist.

The second embodiment of the present disclosure has been described above.

4-3. Third Embodiment

Subsequently, a third embodiment of the present disclosure will be described.

Figure 14:
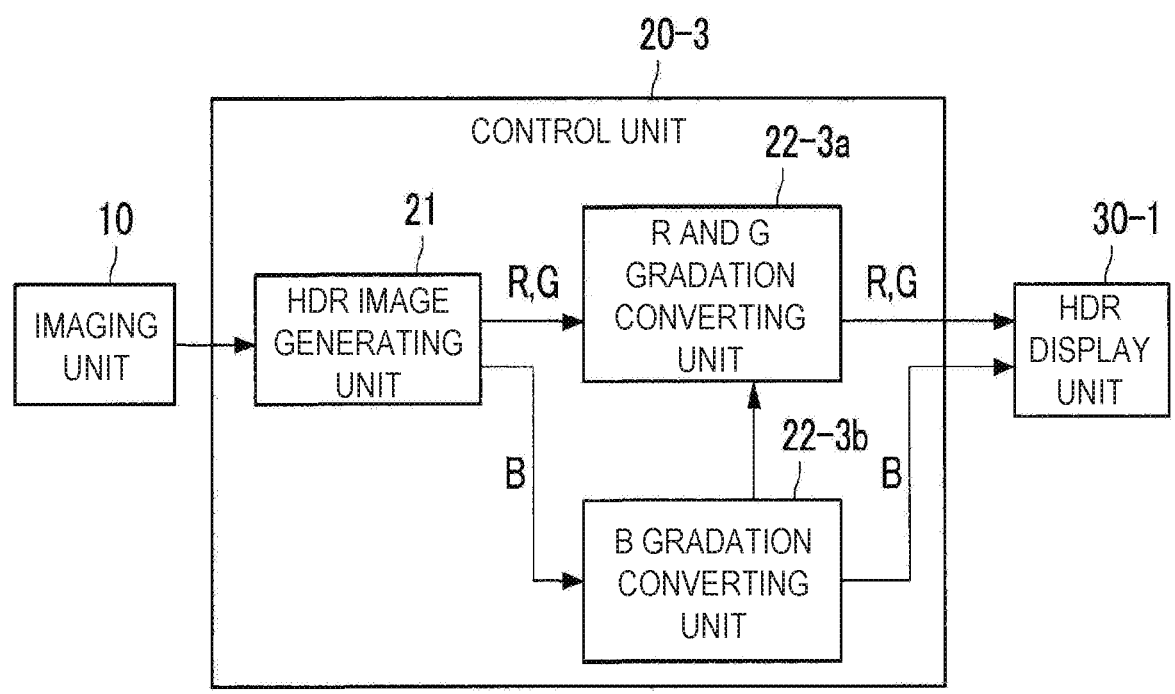
FIG. 14 is a view illustrating a configuration example of a control unit according to a third embodiment of the present disclosure.

FIG. 14 is a view illustrating a configuration example of a control unit 20-3 according to the third embodiment of the present disclosure. As illustrated in FIG. 14, the control unit 20-3 according to the third embodiment of the present disclosure differs from the control unit 20 illustrated in FIG. 7 in that an R and G gradation converting unit 22-3a and a B gradation converting unit 22-3b are provided in place of the gradation converting unit 22. Therefore, in the following description, among the control unit 20-3 according to the third embodiment of the present disclosure, the R and G gradation converting unit 22-3a and the B gradation converting unit 22-3b will be mainly described, and detailed description of other configurations will be omitted.

Here, eyes of a human tend to feel glare for light having a wavelength from 380 nm to 500 nm. This wavelength is a region of blue. Therefore, in the third embodiment, a case of making the user less likely to feel glare by making a blue component in a high brightness portion of the endoscope image darker than other colors will be described.

The B gradation converting unit 22-3b adjusts gradation for a pixel signal of a specific color among the HDR image (first image signal) obtained by the HDR image generating unit 21. More specifically, the B gradation converting unit 22-3b performs gradation compression for the B signal among three color components of red (R), green (G) and blue (B) which constitute the HDR image (first image signal).

The R and G gradation converting unit 22-3a performs gradation compression on the pixel signals of colors other than the specific color more weakly than gradation compression to be performed on the image signal of the specific color by the B gradation converting unit 22-3b or does not adjust gradation for the pixel signals of colors other than the specific color. More specifically, the R and G gradation converting unit 22-3a performs gradation compression on the R signal and the G signal more weakly than gradation compression to be performed on the B signal among three color components of red (R), green (G) and blue (B) which constitute the HDR image (first image signal) or does not perform gradation compression on the R signal and the G signal.

Figure 15:
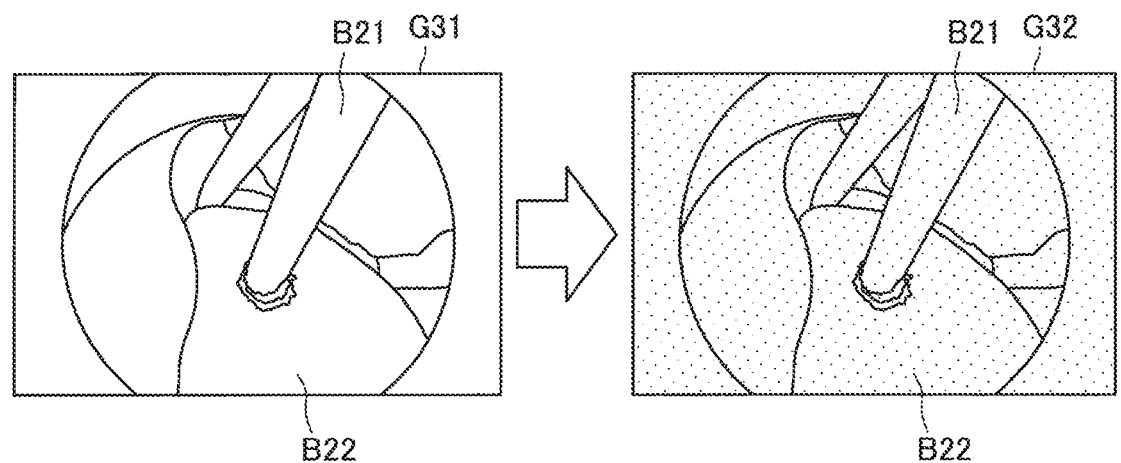
FIG. 15 is a view illustrating examples of endoscope images before and after gradation compression is performed for a B signal.

FIG. 15 is a view illustrating examples of the endoscope images before and after gradation compression is performed for the B signal. An endoscope image G31 is an endoscope image before gradation compression is performed for the B signal. The endoscope image G32 is an endoscope image after gradation compression is performed for the B signal.

Compared to the endoscope image before gradation compression is performed for the B signal, the endoscope image after gradation compression is performed for the B signal becomes an image which is eye-friendly as a result of glare being reduced though colors are not truly reproduced.

Figure 16:
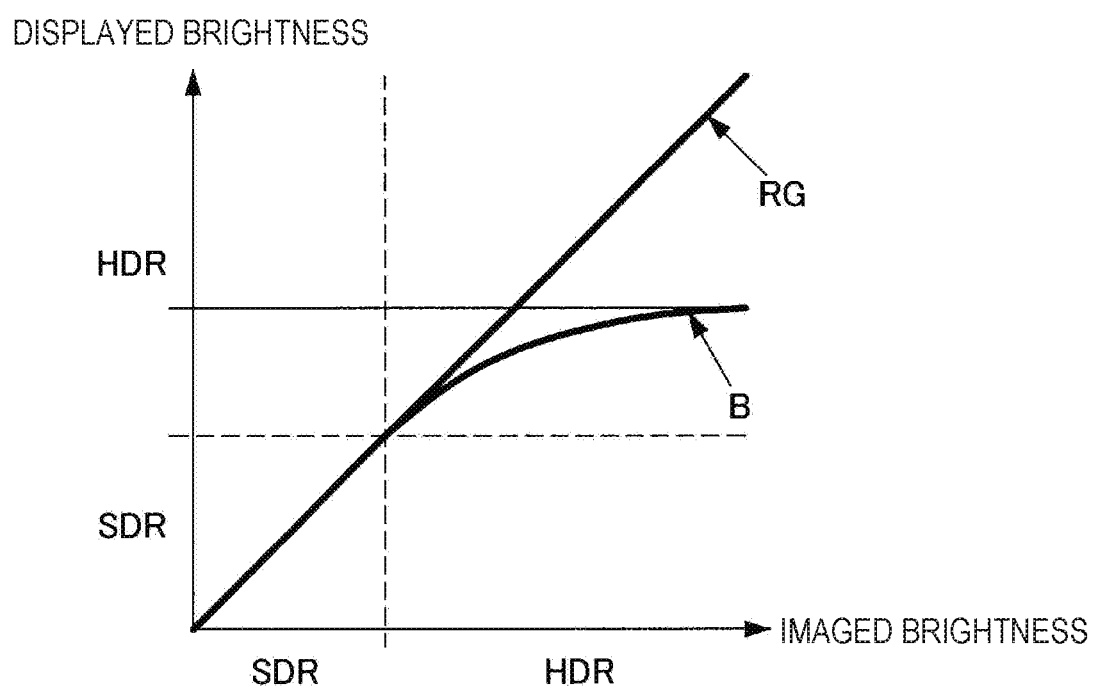
FIG. 16 is a view illustrating examples of an RG signal for which gradation is not adjusted, and the B signal after gradation is adjusted.

FIG. 16 is a view illustrating an example of the RG signal for which gradation is not adjusted and the B signal after gradation is adjusted. As illustrated in FIG. 16, by gradation compression being performed for the B signal, glare by a high-brightness blue component is reduced compared to an image before gradation compression is performed for the B signal.

The third embodiment of the present disclosure has been described above.

4-4. Fourth Embodiment

Subsequently, a fourth embodiment of the present disclosure will be described.

Figure 17:
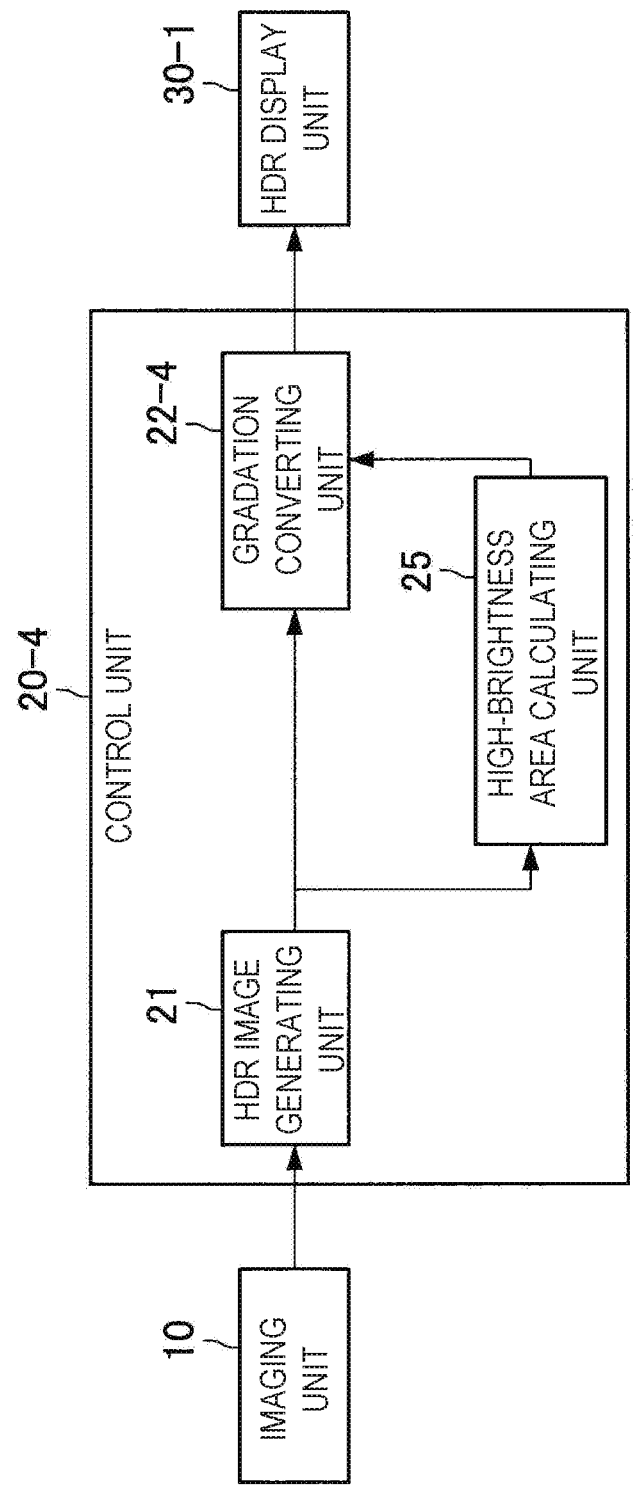
FIG. 17 is a view illustrating a configuration example of a control unit according to a fourth embodiment of the present disclosure.

FIG. 17 is a view illustrating a configuration example of a control unit 20-4 according to the fourth embodiment of the present disclosure. As illustrated in FIG. 17, the control unit 20-4 according to the fourth embodiment of the present disclosure differs from the control unit 20 illustrated in FIG. 7 in that a high-brightness area calculating unit 25 is provided, and a gradation converting unit 22-4 is provided in place of the gradation converting unit 22. Therefore, in the following description, the high-brightness area calculating unit 25 and the gradation converting unit 22-4 will be mainly described among the control unit 20-4 according to the fourth embodiment of the present disclosure, and detailed description of other configurations will be omitted.

Here, eyes of a human tend to be more likely to feel glare as an area of an extremely bright region in the image is larger. Therefore, in the fourth embodiment of the present disclosure, a case will be described where an extremely bright region in the endoscope image is calculated, and gradation of the endoscope image is adjusted on the basis of the calculation result. More specifically, in the fourth embodiment of the present disclosure, a case will be mainly described where an area of an extremely bright region in the endoscope image is calculated, and gradation adjustment of controlling a maximum value of brightness in accordance with the calculated area is performed.

The high-brightness area calculating unit 25 calculates an area of an extremely bright portion in the HDR image (first image signal) obtained by the HDR image generating unit 21. As a method for calculating an area of an extremely bright portion, for example, it is possible to employ a method in which the number of pixels for which brightness values are greater than a certain threshold (second brightness value) is calculated. In the following description, the number of pixels for which brightness values are greater than a certain threshold (second brightness value) will be also simply referred to as a "high-brightness area".

The gradation converting unit 22-4 adjusts gradation for the HDR image (first image signal) on the basis of pixels for which brightness is greater than the second brightness value among the HDR image (first image signal) obtained by the HDR image generating unit 21. More specifically, the gradation converting unit 22-4 determines a maximum value of brightness (first brightness value) on the basis of the number of pixels for which brightness is greater than the second brightness value among the HDR image (first image signal) and adjusts gradation so that the brightness values of all the pixel signals of the HDR image (first image signal) become equal to or less than the maximum value of brightness.

Figure 18:
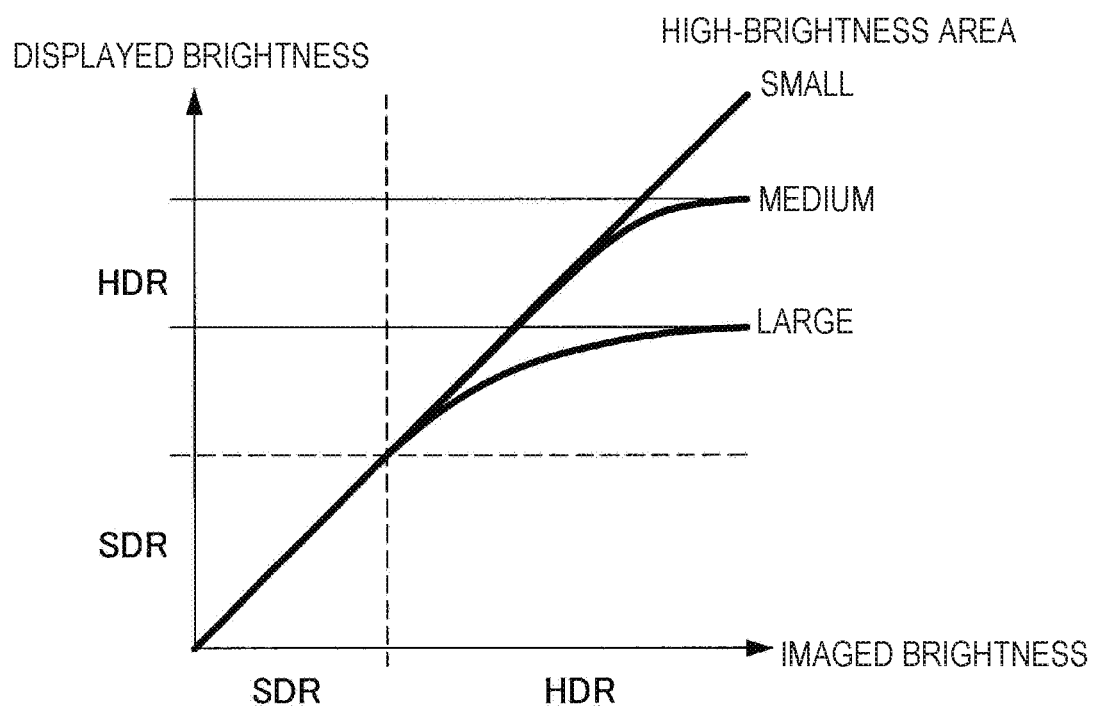
FIG. 18 is a view illustrating examples of output images after gradation is adjusted in accordance with respective high brightness areas.

FIG. 18 is a view illustrating examples of output images after gradation is adjusted in accordance with respective high-brightness areas. Referring to FIG. 18, examples of output images respectively corresponding to high-brightness areas of "small", "medium" and "large" are presented. As indicated with the high-brightness areas of "medium" and "large", it would be better that the gradation converting unit 22-4 performs gradation compression more intensely to reduce glare as the high-brightness area is larger, by lowering the maximum value of brightness. Further, as indicated with the high-brightness area of "small", the gradation converting unit 22-4 does not have to perform gradation compression in a case where the high-brightness area is smaller than a certain area.

The fourth embodiment of the present disclosure has been described above.

4-5. Fifth Embodiment

Subsequently, a fifth embodiment of the present disclosure will be described.

Figure 19:
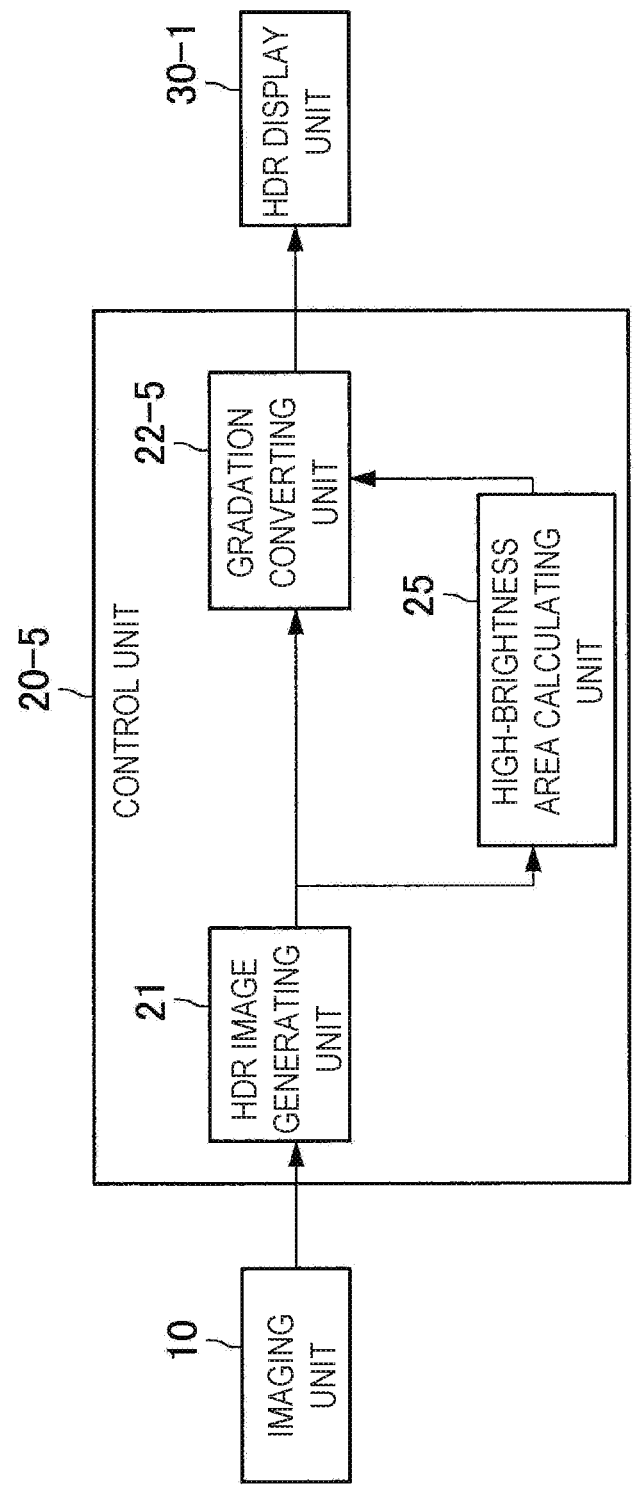
FIG. 19 is a view illustrating a configuration example of a control unit according to a fifth embodiment of the present disclosure.

FIG. 19 is a view illustrating a configuration example of a control unit 20-5 according to the fifth embodiment of the present disclosure. As illustrated in FIG. 19, the control unit 20-5 according to the fifth embodiment of the present disclosure differs from the control unit 20-4 illustrated in FIG. 17 in that a gradation converting unit 22-5 is provided in place of the gradation converting unit 22-4. Therefore, in the following description, the gradation converting unit 22-5 will be mainly described among the control unit 20-5 according to the fifth embodiment of the present disclosure, and detailed description of other configurations will be omitted.

Eyes of a human have characteristics that pupils are closed when eyes look at an extremely bright portion, so that it becomes easy to see a bright portion, while it becomes difficult to see a dark portion. By this means, if there are a number of extremely bright portions in the HDR image captured with the endoscope, there is a possibility that pupils of the user who watches the image are closed, and it becomes difficult to see a dark portion in the image. Therefore, in the fifth embodiment of the present disclosure, a case will be mainly described where an area of an extremely bright region in the endoscope image is calculated, and gradation adjustment of making it easier to see a dark portion is performed in accordance with the calculated area.

The gradation converting unit 22-5 makes brightness of pixel signals for which brightness is smaller than a third brightness value among the HDR image (first image signal) greater in a case where the number of pixels for which brightness is greater than the second brightness value among the HDR image (first image signal) obtained by the HDR image generating unit 21 is larger than a predetermined number.

Figure 20:
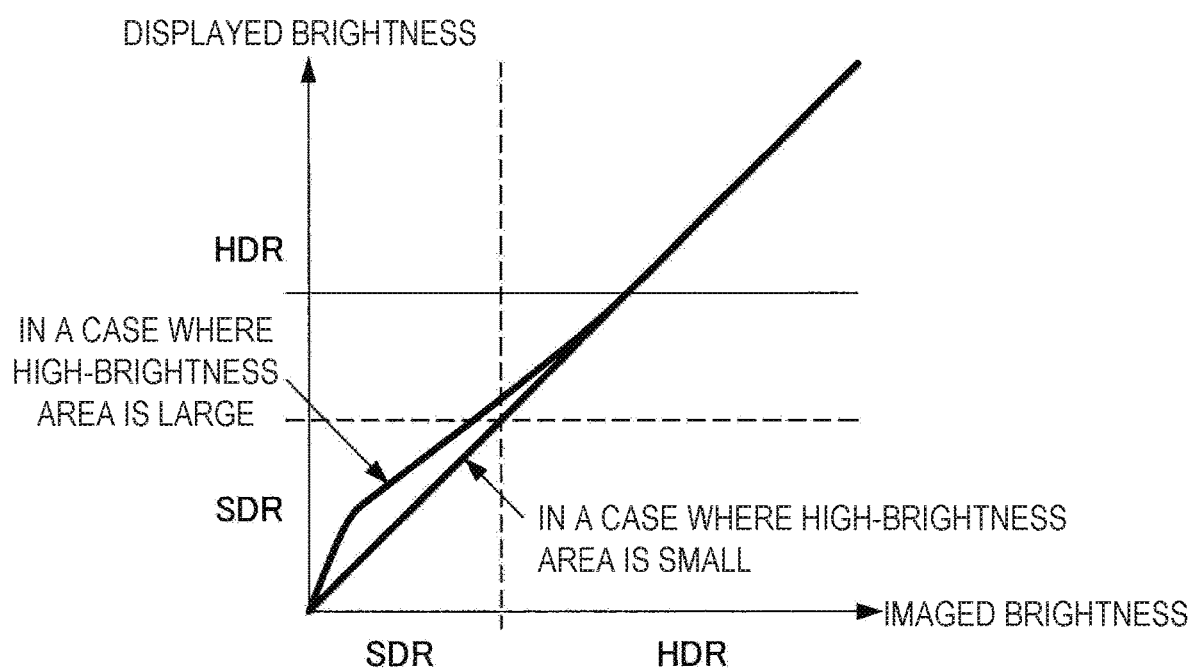
FIG. 20 is a view illustrating examples of output images after gradation is adjusted in accordance with respective high brightness areas.

FIG. 20 is a view illustrating examples of the output images after gradation adjustment is performed in accordance with respective high-brightness areas. Referring to FIG. 20, the examples of the output images respectively corresponding to high-brightness areas of "small", "large" are presented. The high-brightness area of "large" corresponds to a case where the number of pixels for which brightness is greater than the second brightness value is larger than a predetermined number. In such a case, the gradation converting unit 22-5 makes brightness of pixel signals for which brightness is smaller than the third brightness value among the HDR image (first image signal) greater. Meanwhile, the high-brightness area of "small" corresponds to a case where the number of pixels for which brightness is greater than the second brightness value is equal to or smaller than the predetermined number. In such a case, the gradation converting unit 22-5 does not have to change brightness of the HDR image (first image signal).

Note that the gradation converting unit 22-5 may change brightness of the dark portion so as to prevent brightness of the dark portion from precipitously changing in accordance with temporal change of the high-brightness area in the endoscope image. That is, the gradation converting unit 22-5 may limit a change amount of brightness of the dark portion so that brightness of the dark portion gently changes in a time direction.

For example, the gradation converting unit 22-5 may make brightness of the pixel signals for which brightness is smaller than the third brightness value greater using the same adjustment amount. The adjustment amount in this event may be determined on the basis of an average amount of the assumed high-brightness area.

Further, the gradation converting unit 22-5 may determine a period (second period) during which the brightness value of the HDR image (first image signal) is maintained at brightness corresponding to a value included within a predetermined range in accordance with a period (first period) during which the brightness value of the HDR image (first image signal) indicates a value within the predetermined range. For example, the gradation converting unit 22-5 may determine a period (second period) during which the brightness value of the HDR image (first image signal) is maintained at brightness corresponding to a value included in a predetermined range to be longer as the period (first period) during which the brightness value of the HDR image (first image signal) indicates a value within the predetermined range is longer.

The fifth embodiment of the present disclosure has been described above.

4-6. Sixth Embodiment

Subsequently, a sixth embodiment of the present disclosure will be described.

Figure 21:
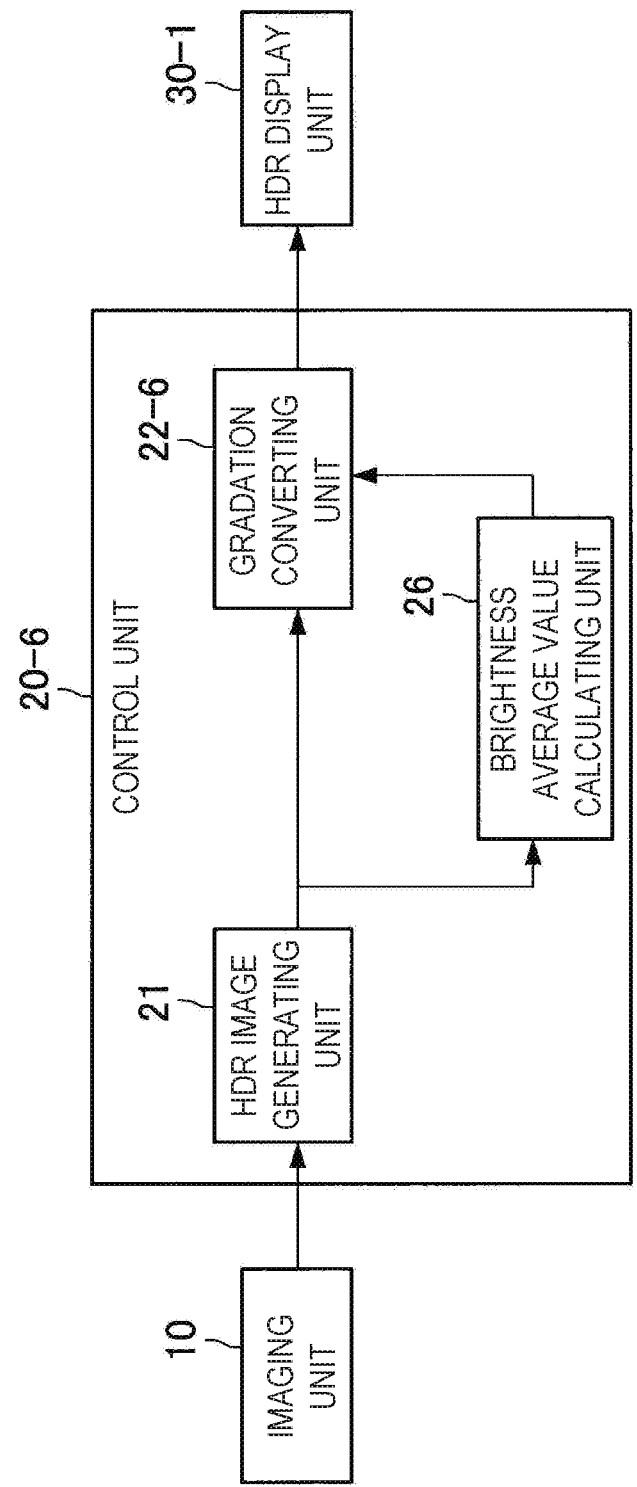
FIG. 21 is a view illustrating a configuration example of a control unit according to a sixth embodiment of the present disclosure.

FIG. 21 is a view illustrating a configuration example of a control unit 20-6 according to the sixth embodiment of the present disclosure. As illustrated in FIG. 21, the control unit 20-6 according to the sixth embodiment of the present disclosure differs from the control unit 20 illustrated in FIG. 7 in that a brightness average value calculating unit 26 is provided, and a gradation converting unit 22-6 is provided in place of the gradation converting unit 22. Therefore, in the following description, the gradation converting unit 22-6 will be mainly described among the control unit 20-6 according to the sixth embodiment of the present disclosure, and detailed description of other configurations will be omitted.

In the fourth embodiment of the present disclosure, a case has been described where an area of an extremely bright region in the endoscope image is calculated, and gradation adjustment of controlling a maximum value of brightness in accordance with the calculated area is performed. Further, in the fifth embodiment of the present disclosure, a case has been described where an area of an extremely bright region in the endoscope image is calculated, and gradation adjustment of making it easier to see a dark portion in accordance with the calculated area is performed.

In a sixth embodiment of the present disclosure, a case will be mainly described where an "average value of brightness" is used in place of the "area of an extremely bright region (high-brightness area)" used in the fourth embodiment of the present disclosure and the fifth embodiment of the present disclosure.

The brightness average value calculating unit 26 calculates an average value of brightness of respective pixel signals constituting the HDR image (first image signal) obtained by the HDR image generating unit 21. Note that, while a case will be mainly assumed where an average value of brightness of the respective pixel signals constituting the HDR image (first image signal) is calculated, the brightness average value calculating unit 26 may calculate an additional value in place of the average value. In this event, in place of the average value, the additional value may be utilized at the gradation converting unit 22-6.

The gradation converting unit 22-6 determines a degree of adjustment of gradation or a region in which gradation is to be adjusted on the basis of an average value of brightness of respective pixel signals constituting the HDR image (first image signal) obtained by the HDR image generating unit 21 and adjusts gradation for the HDR image (first image signal) on the basis of the determined degree of adjustment of gradation or the determined region in which gradation is to be adjusted.

Figure 22:
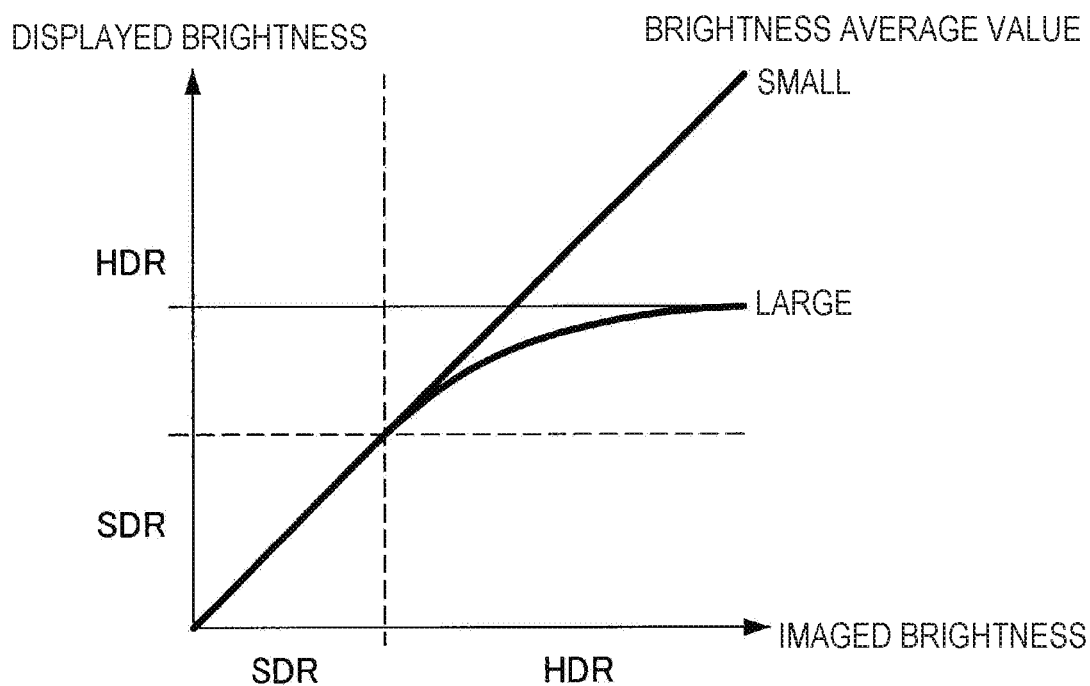
FIG. 22 is a view illustrating examples of output images after gradation is adjusted in accordance with respective brightness average values.

FIG. 22 is a view illustrating examples of the output images after gradation is adjusted in accordance with the respective brightness average values. Referring to FIG. 22, examples of output images respectively corresponding to the average brightness values of "small" and "large" are presented. It would be better that the gradation converting unit 22-6 performs gradation compression intensely to reduce glare by making the maximum value of brightness smaller as the average brightness value is greater. Further, as indicated with the brightness average value of "small", the gradation converting unit 22-6 does not have to perform gradation compression in a case where the average brightness value is smaller than a certain brightness value.

Note that, while a case has been assumed here where brightness values of all the pixel signals of the HDR image (first image signal) are adjusted, a region in which gradation is to be adjusted does not have to be all the pixels of the HDR image (first image signal), and may be pixels of part of the HDR image (first image signal). In this event, the region in which gradation is to be adjusted may be fixedly determined to be a predetermined region (such as, for example, a central region) in the HDR image (first image signal).

The gradation converting unit 22-6 may determine a region in which gradation is to be adjusted on the basis of an average value of brightness of respective pixel signals constituting the HDR image (first image signal) and may adjust gradation of the HDR image (first image signal) on the basis of the determined region in which gradation is to be adjusted. For example, the gradation converting unit 22-6 may determine a narrower region in which gradation is to be adjusted as an average value of brightness of respective pixel signals is smaller.

The sixth embodiment of the present disclosure has been described above.

4-7. Seventh Embodiment

Subsequently, a seventh embodiment of the present disclosure will be described.

Figure 23:
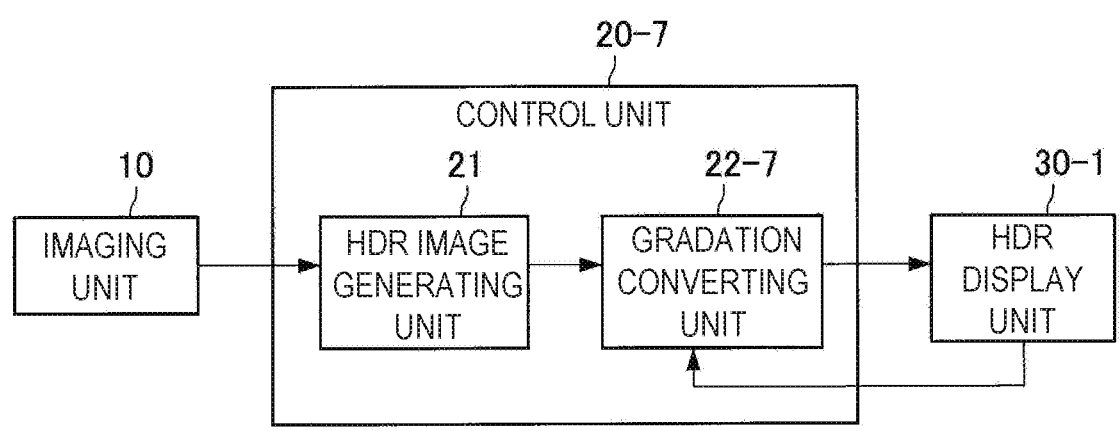
FIG. 23 is a view illustrating a configuration example of a control unit according to a seventh embodiment of the present disclosure.

FIG. 23 is a view illustrating a configuration example of a control unit 20-7 according to the seventh embodiment of the present disclosure. As illustrated in FIG. 23, the control unit 20-7 according to the seventh embodiment of the present disclosure differs from the control unit 20 illustrated in FIG. 7 in that a gradation converting unit 22-7 is provided in place of the gradation converting unit 22. Therefore, in the following description, the gradation converting unit 22-7 will be mainly described among the control unit 20-7 according to the seventh embodiment of the present disclosure, and detailed description of other configurations will be omitted.

Here, brightness of the output image displayed at the HDR display unit 30-1 changes in accordance with brightness setting information of the HDR display unit 30-1. For example, as brightness of the HDR display unit 30-1 is set higher, a bright portion of the endoscope image displayed at the HDR display unit 30-1 increases, and the user is more likely to feel glare. Therefore, in the seventh embodiment of the present disclosure, a case will be mainly described where gradation adjustment for reducing glare is performed on the basis of the brightness setting information of the HDR display unit 30-1.

The gradation converting unit 22-7 acquires the brightness setting information of the HDR display unit 30-1 and adjusts gradation for the HDR image (first image signal) on the basis of the brightness setting information of the HDR display unit 30-1. More specifically, it would be better that the gradation converting unit 22-7 starts gradation compression from a region in which brightness is smaller as brightness setting of the HDR display unit 30-1 is brighter. Note that, as illustrated in FIG. 23, the gradation converting unit 22-7 is only required to acquire the brightness setting information from the HDR display unit 30-1 in a case where the HDR display unit 30-1 operates on the basis of the brightness setting information set for the HDR display unit 30-1.

Figure 24:
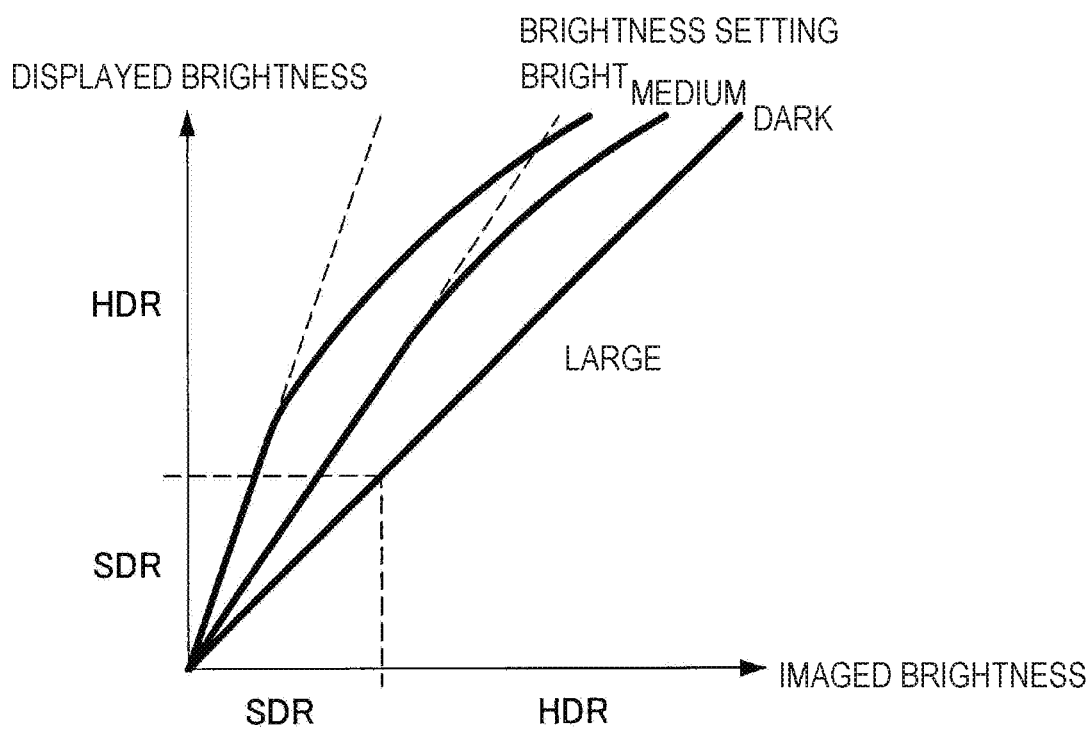
FIG. 24 is a view illustrating examples of output images after gradation is adjusted in accordance with respective pieces of brightness setting information.

FIG. 24 is a view illustrating examples of the output images after gradation is adjusted in accordance with respective pieces of brightness setting information. Referring to FIG. 24, examples of output images respectively corresponding to brightness setting of "bright", "medium" and "dark" are presented. As indicated with the brightness setting of "bright" and "medium", it would be better that the gradation converting unit 22-7 starts gradation compression from a region where brightness is smaller as brightness setting is brighter. Further, as indicated with the brightness setting of "dark", the gradation converting unit 22-7 does not have to perform gradation compression in a case where brightness setting is darker than predetermined brightness.

The seventh embodiment of the present disclosure has been described above.

4-8. Eighth Embodiment

Subsequently, an eighth embodiment of the present disclosure will be described.

Figure 25:
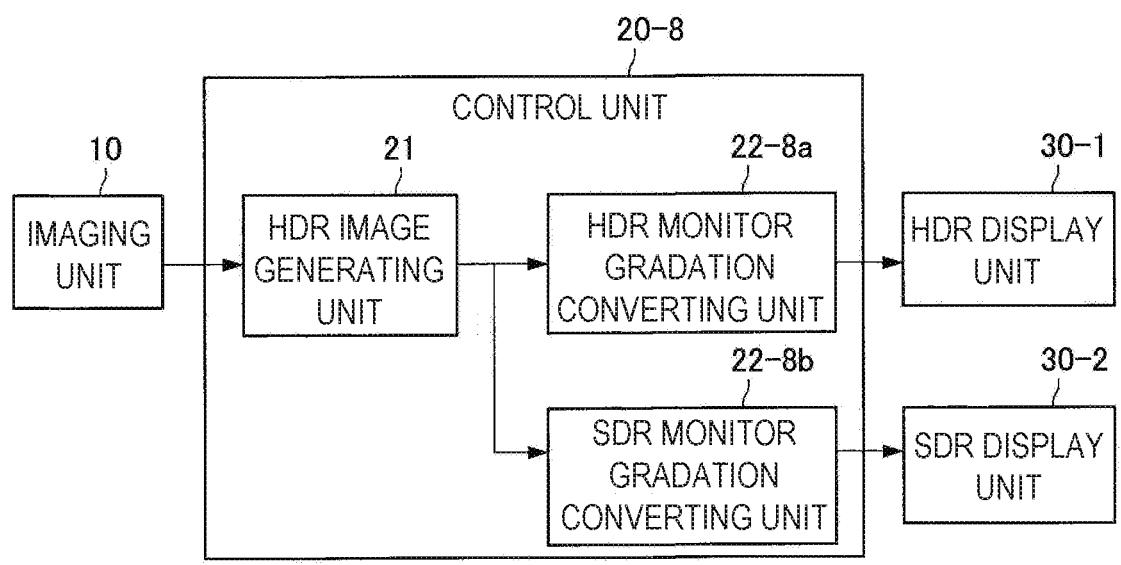
FIG. 25 is a view illustrating a configuration example of a control unit according to a first example of an eighth embodiment of the present disclosure.

FIG. 25 is a view illustrating a configuration example of a control unit 20-8 according to the first example of the eighth embodiment of the present disclosure. As illustrated in FIG. 25, the control unit 20-8 according to the first example of the eighth embodiment of the present disclosure differs from the control unit 20 illustrated in FIG. 7 in that an HDR monitor gradation converting unit 22-8a and an SDR monitor gradation converting unit 22-8b are provided in place of the gradation converting unit 22. Therefore, in the following description, among the control unit 20-8 according to the first example of the eighth embodiment of the present disclosure, the HDR monitor gradation converting unit 22-8a and the SDR monitor gradation converting unit 22-8b will be mainly described, and detailed description of other configurations will be omitted.

Here, there is a case where an SDR monitor (SDR display unit 30-2) is connected to the control unit 20-8 as other sub-monitors even if a main monitor through which the user watches the endoscope image is an HDR monitor (HDR display unit 30-1). In this case, even if an image which is the same as the image for which gradation is adjusted so as to conform to the HDR monitor is output to the SDR monitor, an appropriate image is not displayed at the SDR monitor. Therefore, in a first example of the eighth embodiment of the present disclosure, a case will be mainly described where gradation adjustment is changed in accordance with types of a monitor to be connected to the control unit 20-8.

In the first example, the control unit 20-8 includes a gradation converting unit for each monitor. The HDR monitor gradation converting unit 22-8a, which is connected to the HDR display unit 30-1, generates an HDR image (second image signal) having a first dynamic range compliant with high-dynamic range standards on the basis of the HDR image (first image signal) obtained by the HDR image generating unit 21.

In this event, the HDR monitor gradation converting unit 22-8a may perform gradation compression for an HDR monitor or does not have to perform gradation compression for the HDR image (first image signal) obtained by the HDR image generating unit 21 as already described in the above-described respective embodiments. The HDR monitor gradation converting unit 22-8a controls the HDR display unit 30-1 so as to output the generated HDR image (second image signal).

The SDR monitor gradation converting unit 22-8b, which is connected to the SDR display unit 30-2, generates an SDR image (third image signal) for which a difference between a maximum value of brightness and a minimum value of brightness is smaller than the first dynamic range on the basis of the HDR image (first image signal) obtained by the HDR image generating unit 21.

In this event, the SDR monitor gradation converting unit 22-8b performs gradation compression for the HDR image (first image signal) obtained by the HDR image generating unit 21 so that the maximum value of brightness falls within the SDR. The SDR monitor gradation converting unit 22-8b controls the SDR display unit 30-2 so as to output the generated SDR image (third image signal).

Figure 26:
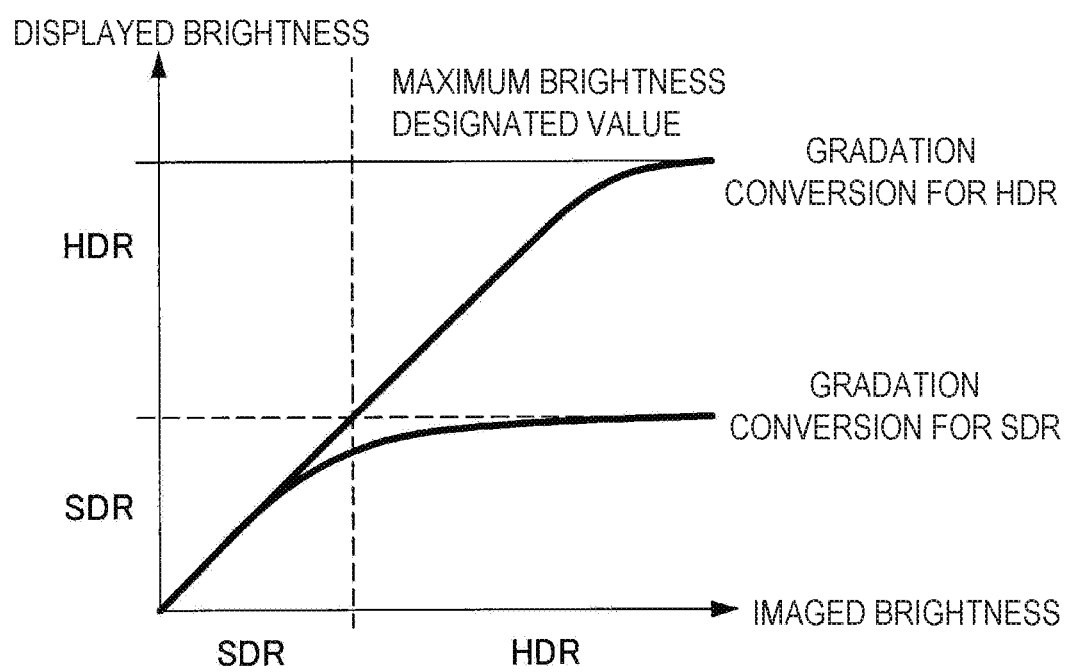
FIG. 26 is a view illustrating examples of output images after gradation conversion for respective monitors is performed.

FIG. 26 is a view illustrating examples of output images after gradation conversion for respective monitors is performed. Referring to FIG. 26, examples of the output image after gradation conversion for the HDR is performed and the output image after gradation conversion for the SDR is performed are presented. In the example illustrated in FIG. 26, as already described in the first embodiment of the present disclosure, the maximum value of brightness is designated as the "maximum brightness designated value" in gradation conversion for the HDR.

Figure 27:
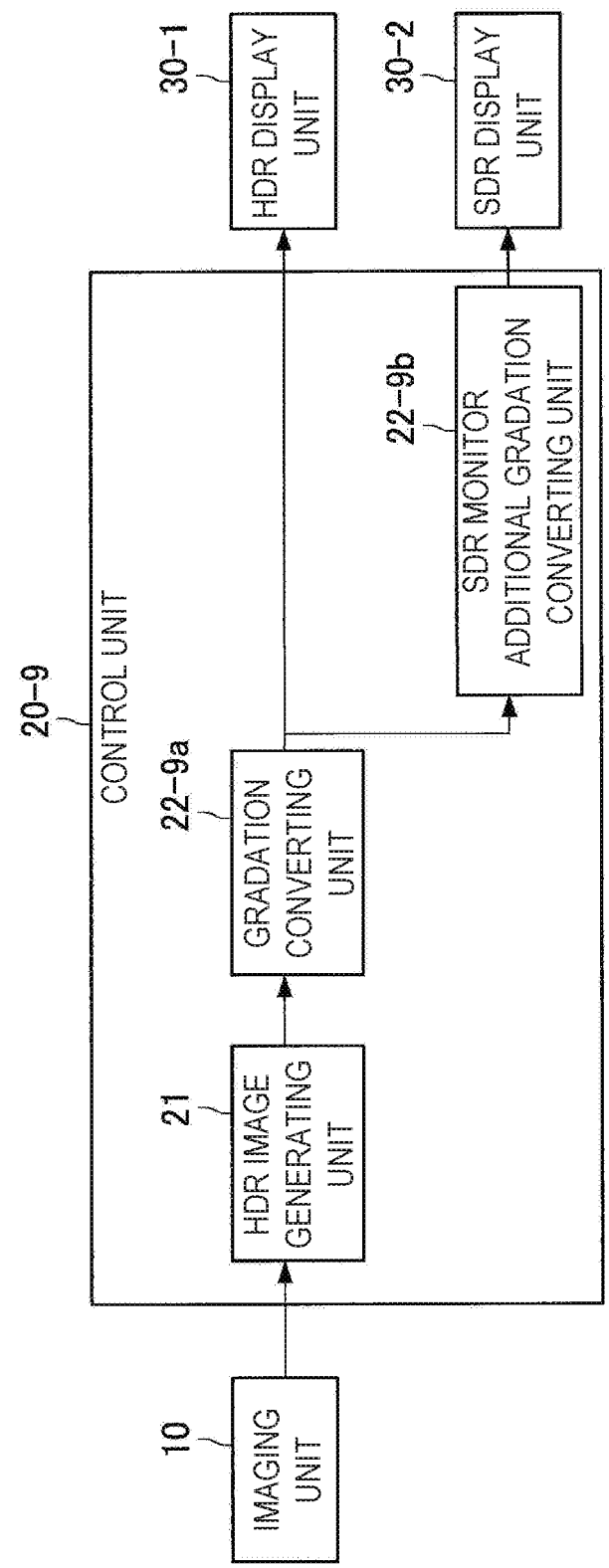
FIG. 27 is a view illustrating a configuration example of a control unit according to a second example of the eighth embodiment of the present disclosure.

FIG. 27 is a view illustrating a configuration example of a control unit 20-9 according to the second example of the eighth embodiment of the present disclosure. As illustrated in FIG. 27, the control unit 20-9 according to the second example of the eighth embodiment of the present disclosure differs from the control unit 20 illustrated in FIG. 7 in that an HDR monitor gradation converting unit 22-9a and an SDR monitor additional gradation converting unit 22-9b are provided in place of the gradation converting unit 22. Therefore, in the following description, among the control unit 20-9 according to the second example of the eighth embodiment of the present disclosure, the gradation converting unit 22-9a and the SDR monitor additional gradation converting unit 22-9b will be mainly described, and detailed description of other configurations will be omitted.

Also in the second example of the eighth embodiment of the present disclosure, a case will be mainly described where gradation adjustment is changed in accordance with types of a monitor to be connected to the control unit 20-9. The gradation converting unit 22-9a, which is connected to the HDR display unit 30-1, generates an HDR image (second image signal) having a first dynamic range compliant with high-dynamic range standards on the basis of the HDR image (first image signal) obtained by the HDR image generating unit 21.

In this event, the gradation converting unit 22-9a may perform gradation compression for an HDR monitor or does not have to perform gradation compression for the HDR image (first image signal) obtained by the HDR image generating unit 21 as already described in the above-described respective embodiments. The gradation converting unit 22-9a controls the HDR display unit 30-1 so as to output the generated HDR image (second image signal). Further, the gradation converting unit 22-9a outputs the generated HDR image (second image signal) also to the SDR monitor additional gradation converting unit 22-9b.

The SDR monitor additional gradation converting unit 22-9b, which is connected to the SDR display unit 30-2, generates an SDR image (third image signal) for which a difference between a maximum value of brightness and a minimum value of brightness is smaller than a dynamic range (first dynamic range) of the HDR image (second image signal) on the basis of the HDR image (second image signal) generated by the gradation converting unit 22-9a.

In this event, the SDR monitor additional gradation converting unit 22-9b performs gradation compression for the HDR image (second image signal) generated by the gradation converting unit 22-9a so that the maximum value of brightness falls within the SDR. The SDR monitor additional gradation converting unit 22-9b controls the SDR display unit 30-2 so as to output the generated SDR image (third image signal).

Figure 28:
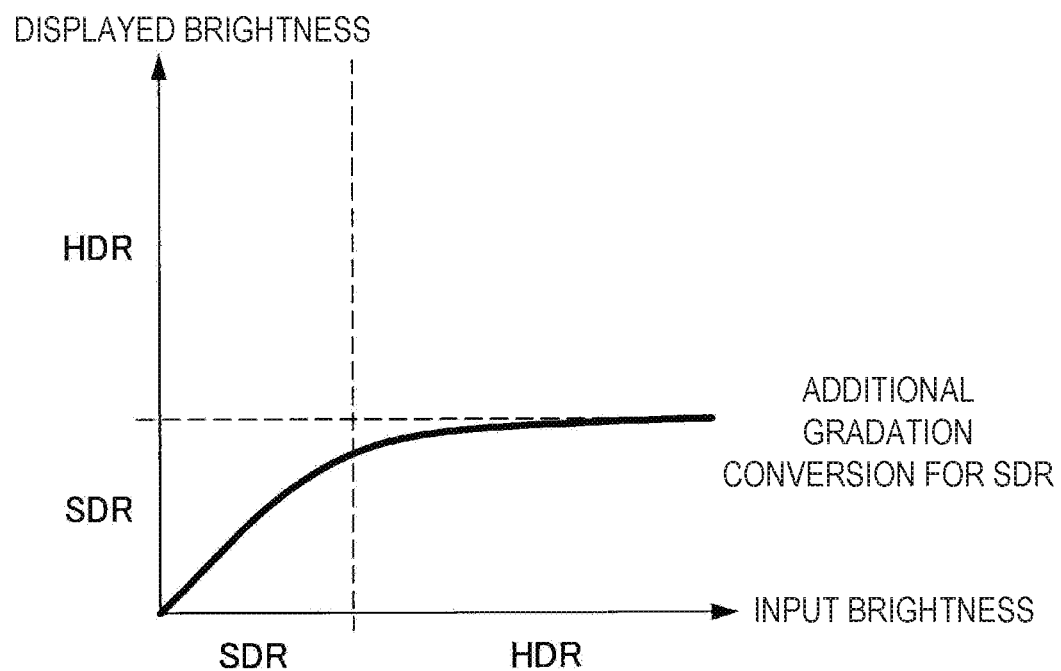
FIG. 28 is a view illustrating an example of an output image after additional gradation conversion for an SDR is performed.

FIG. 28 is a view illustrating an example of an output image after additional gradation conversion for the SDR is performed. Referring to FIG. 28, brightness of the HDR image (second image signal) generated by the gradation converting unit 22-9a is indicated as "input brightness", and brightness of the output image after additional gradation conversion for the SDR is performed is indicated as "displayed brightness". As illustrated in FIG. 28, the SDR monitor additional gradation converting unit 22-9b performs gradation compression for the HDR image (second image signal) generated by the gradation converting unit 22-9a so that the maximum value of brightness falls within the SDR.

Figure 29:
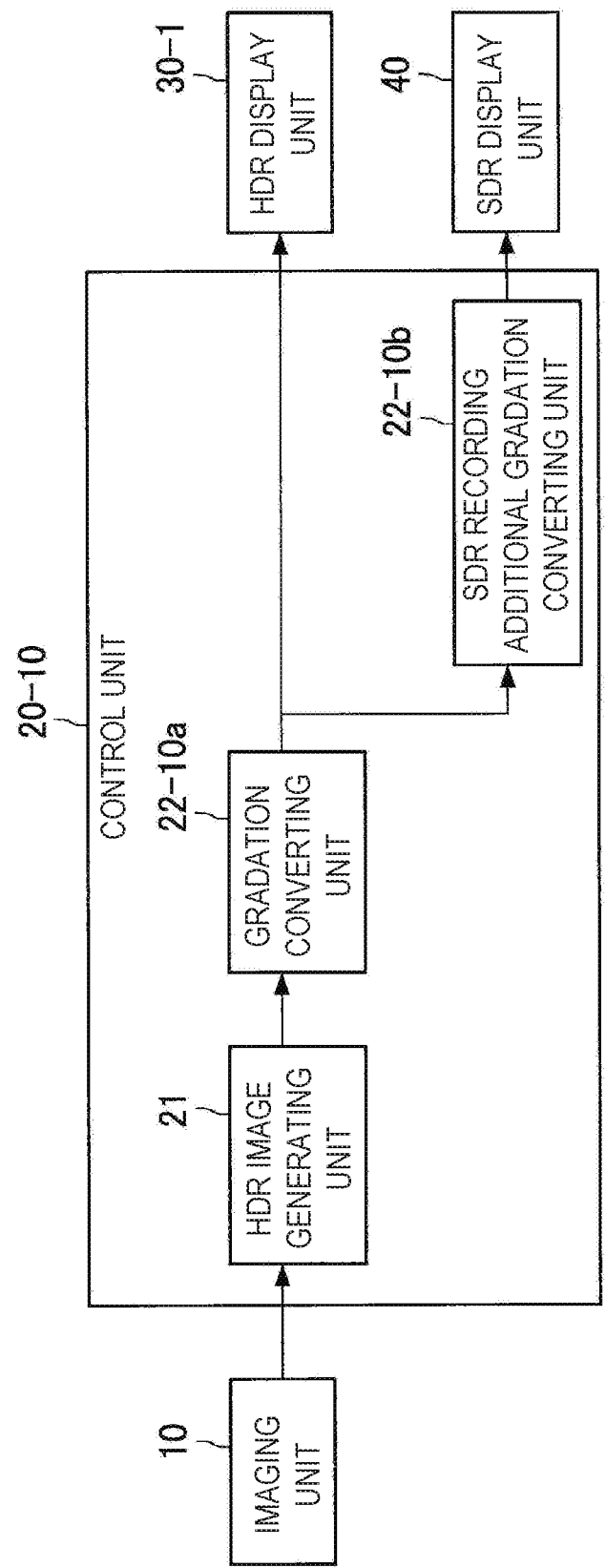
FIG. 29 is a view illustrating a configuration example of a control unit according to a third example of the eighth embodiment of the present disclosure.

FIG. 29 is a view illustrating a configuration example of a control unit 20-10 according to the third example of the eighth embodiment of the present disclosure. As illustrated in FIG. 29, the control unit 20-10 according to the third example of the eighth embodiment of the present disclosure differs from the control unit 20 illustrated in FIG. 7 in that a gradation converting unit 22-10a and an SDR recording additional gradation converting unit 22-10 are provided in place of the gradation converting unit 22. Therefore, in the following description, among the control unit 20-10 according to the third example of the eighth embodiment of the present disclosure, the gradation converting unit 22-10a and an SDR recording additional gradation converting unit 22-10b will be mainly described, and detailed description of other configurations will be omitted.

Here, there is a case where a recorder is connected to the control unit 20-10. As illustrated in FIG. 29, in a case where a recorder connected to the control unit 20-1 is a recorder for an SDR (SDR recording unit 40), in a similar manner to a case where the SDR display unit 30-2 is connected to the control unit 20-8 as illustrated in the second example of the eighth embodiment of the present disclosure, additional gradation conversion for SDR recording is only required to be performed by the SDR recording additional gradation converting unit 20-10b (the SDR recording additional gradation converting unit 22-10b is only required to have functions similar to those of the SDR monitor additional gradation converting unit 22-9b illustrated in FIG. 27). Note that the gradation converting unit 22-10a is also only required to have functions similar to those of the gradation converting unit 22-9a illustrated in FIG. 27.

The eighth embodiment of the present disclosure has been described above.

5. Application Example

An example of the endoscopic surgery system 5000 to which the technology according to an embodiment of the present disclosure can be applied has been described above. It is to be noted here that, although the endoscopic surgery system 5000 has been described as an example, the system to which the technology according to an embodiment of the present disclosure can be applied is not limited to the example. For example, the technology according to an embodiment of the present disclosure may be applied to a flexible endoscopic system for inspection or a microscopic surgery system. Hereinafter, the endoscopic surgery system to which the technology according to the present disclosure may be applied will be described.

FIG. 30 is a view illustrating an example of a schematic configuration of a microscopic surgery system 5300 to which the technology according to an embodiment of the present disclosure can be applied. Referring to FIG. 30, the microscopic surgery system 5300 includes a microscope apparatus 5301, a control apparatus 5317 and a display apparatus 5319. It is to be noted that, in the description of the microscopic surgery system 5300, the term "user" signifies an arbitrary one of medical staff members such as a surgery or an assistant who uses the microscopic surgery system 5300.

The microscope apparatus 5301 has a microscope unit 5303 for enlarging an observation target (surgical region of a patient) for observation, an arm unit 5309 which supports the microscope unit 5303 at a distal end thereof, and a base unit 5315 which supports a proximal end of the arm unit 5309.

The microscope unit 5303 includes a cylindrical portion 5305 of a substantially cylindrical shape, an imaging unit (not illustrated) provided in the inside of the cylindrical portion 5305, and an operation unit 5307 provided in a partial region of an outer circumference of the cylindrical portion 5305. The microscope unit 5303 is a microscope unit of the electronic imaging type (microscope unit of the so-called video type) which picks up an image electronically by the imaging unit.

A cover glass member for protecting the internal imaging unit is provided at an opening face of a lower end of the cylindrical portion 5305. Light from an observation target (hereinafter referred to also as observation light) passes through the cover glass member and enters the imaging unit in the inside of the cylindrical portion 5305. It is to be noted that a light source which includes, for example, a light emitting diode (LED) or the like may be provided in the inside of the cylindrical portion 5305, and upon image picking up, light may be irradiated upon an observation target from the light source through the cover glass member.

The imaging unit includes an optical system which condenses observation light, and an imaging element which receives the observation light condensed by the optical system. The optical system includes a combination of a plurality of lenses including a zoom lens and a focusing lens. The optical system has optical properties adjusted such that the observation light is condensed to be formed image on a light receiving face of the imaging element. The imaging element receives and photoelectrically converts the observation light to generate a signal corresponding to the observation light, namely, an image signal corresponding to an observation image. As the imaging element, for example, an imaging element which has a Bayer array and is capable of picking up an image in color is used. The imaging element may be any of various known imaging elements such as a complementary metal oxide semiconductor (CMOS) image sensor or a charge coupled device (CCD) image sensor. The image signal generated by the imaging element is transmitted as RAW data to the control apparatus 5317. Here, the transmission of the image signal may be performed suitably by optical communication. This is because, since, at a surgery site, the surgeon performs surgery while observing the state of an affected area through a picked up image, in order to achieve surgery with a higher degree of safety and certainty, it is demanded for a moving image of the surgical region to be displayed on the real time basis as far as possible. Where optical communication is used to transmit the image signal, the picked up image can be displayed with low latency.

It is to be noted that the imaging unit may have a driving mechanism for moving the zoom lens and the focusing lens of the optical system thereof along the optical axis. Where the zoom lens and the focusing lens are moved suitably by the driving mechanism, the magnification of the picked up image and the focal distance upon image picking up can be adjusted. Further, the imaging unit may incorporate therein various functions which may be provided generally in a microscopic unit of the electronic imaging such as an auto exposure (AE) function or an auto focus (AF) function.

Further the imaging unit may be configured as an imaging unit of the single-plate type which includes a single imaging element or may be configured as an imaging unit of the multi-plate type which includes a plurality of imaging elements. Where the imaging unit is configured as that of the multi-plate type, for example, image signals corresponding to red, green, and blue colors may be generated by the imaging elements and may be synthesized to obtain a color image. Alternatively, the imaging unit may be configured such that it has a pair of imaging elements for acquiring image signals for the right eye and the left eye compatible with a stereoscopic vision (three dimensional (3D) display). Where 3D display is applied, the surgeon can comprehend the depth of a living body tissue in the surgical region with a higher degree of accuracy. It is to be noted that, if the imaging unit is configured as that of multi-plate type, then a plurality of optical systems is provided corresponding to the individual imaging elements.

The operation unit 5307 includes, for example, a cross lever, a switch or the like and accepts an operation input of the user. For example, the user can input an instruction to change the magnification of the observation image and the focal distance to the observation target through the operation unit 5307. The magnification and the focal distance can be adjusted by the driving mechanism of the imaging unit suitably moving the zoom lens and the focusing lens in accordance with the instruction. Further, for example, the user can input an instruction to switch the operation mode of the arm unit 5309 (an all-free mode and a fixed mode hereinafter described) through the operation unit 5307. It is to be noted that in a case where the user intends to move the microscope unit 5303, it is supposed that the user moves the microscope unit 5303 in a state in which the user grasps the microscope unit 5303 holding the cylindrical portion 5305. Accordingly, the operation unit 5307 is preferably provided at a position at which it can be operated readily by the fingers of the user with the cylindrical portion 5305 held such that the operation unit 5307 can be operated even while the user is moving the cylindrical portion 5305.

The arm unit 5309 is configured such that a plurality of links (first link 5313*a* to sixth link 5313*f*) is connected for rotation relative to each other by a plurality of joint units (first joint unit 5311*a* to sixth joint unit 5311*f*).

The first joint unit 5311*a* has a substantially columnar shape and supports, at a distal end thereof, an upper end of the cylindrical portion 5305 of the microscope unit 5303 for rotation around an axis of rotation (first axis $O_1$) parallel to the center axis of the cylindrical portion 5305. Here, the first joint unit 5311*a* may be configured such that the first axis $O_1$ thereof is in alignment with the optical axis of the imaging unit of the microscope unit 5303. By the configuration, if the microscope unit 5303 is rotated around the first axis $O_1$, then the field of view can be changed so as to rotate the picked up image.

The first link 5313*a* fixedly supports, at a distal end thereof, the first joint unit 5311*a*. Specifically, the first link 5313*a* is a bar-like member having a substantially L shape and is connected to the first joint unit 5311*a* such that one side at the distal end side thereof extends in a direction orthogonal to the first axis $O_1$ and an end portion of the one side abuts with an upper end portion of an outer periphery of the first joint unit 5311*a*. The second joint unit 5311*b* is connected to an end portion of the other side on the proximal end side of the substantially L shape of the first link 5313*a*.

The second joint unit 5311*b* has a substantially columnar shape and supports, at a distal end thereof, a proximal end of the first link 5313*a* for rotation around an axis of rotation (second axis $O_2$) orthogonal to the first axis $O_1$. The second link 5313*b* is fixedly connected at a distal end thereof to a proximal end of the second joint unit 5311*b*.

The second link 5313*b* is a bar-like member having a substantially L shape, and one side of a distal end side of the second link 5313*b* extends in a direction orthogonal to the second axis $O_2$ and an end portion of the one side is fixedly connected to a proximal end of the second joint unit 5311*b*. The third joint unit 5311*c* is connected to the other side at the proximal end side of the substantially L shape of the second link 5313*b*.

The third joint unit 5311*c* has a substantially columnar shape and supports, at a distal end thereof, a proximal end of the second link 5313*b* for rotation around an axis of rotation (third axis $O_3$) orthogonal to the first axis $O_1$ and the second axis $O_2$. The third link 5313*c* is fixedly connected at a distal end thereof to a proximal end of the third joint unit 5311*c*. By rotating the components at the distal end side including the microscope unit 5303 around the second axis $O_2$ and the third axis $O_3$, the microscope unit 5303 can be moved such that the position of the microscope unit 5303 is changed within a horizontal plane. In other words, by controlling the rotation around the second axis $O_2$ and the third axis $O_3$, the field of view of the picked up image can be moved within a plane.

The third link 5313c is configured such that the distal end side thereof has a substantially columnar shape, and a proximal end of the third joint unit 5311c is fixedly connected to the distal end of the columnar shape such that both of them have a substantially same center axis. The proximal end side of the third link 5313c has a prismatic shape, and the fourth joint unit 5311d is connected to an end portion of the third link 5313c.

The fourth joint unit 5311d has a substantially columnar shape and supports, at a distal end thereof, a proximal end of the third link 5313c for rotation around an axis of rotation (fourth axis $O_4$) orthogonal to the third axis $O_3$. The fourth link 5313d is fixedly connected at a distal end thereof to a proximal end of the fourth joint unit 5311d.

The fourth link 5313d is a bar-like member extending substantially linearly and is fixedly connected to the fourth joint unit 5311d such that it extends orthogonally to the fourth axis $O_4$ and abuts at an end portion of the distal end thereof with a side face of the substantially columnar shape of the fourth joint unit 5311d. The fifth joint unit 5311e is connected to a proximal end of the fourth link 5313d.

The fifth joint unit 5311e has a substantially columnar shape and supports, at a distal end side thereof, a proximal end of the fourth link 5313d for rotation around an axis of rotation (fifth axis $O_5$) parallel to the fourth axis $O_4$. The fifth link 5313e is fixedly connected at a distal end thereof to a proximal end of the fifth joint unit 5311e. The fourth axis $O_4$ and the fifth axis $O_5$ are axes of rotation around which the microscope unit 5303 can be moved in the upward and downward direction. By rotating the components at the distal end side including the microscope unit 5303 around the fourth axis $O_4$ and the fifth axis $O_5$, the height of the microscope unit 5303, namely, the distance between the microscope unit 5303 and an observation target, can be adjusted.

The fifth link 5313e includes a combination of a first member having a substantially L shape one side of which extends in the vertical direction and the other side of which extends in the horizontal direction, and a bar-like second member extending vertically downwardly from the portion of the first member which extends in the horizontal direction. The fifth joint unit 5311e is fixedly connected at a proximal end thereof to a neighboring upper end of a part extending the first member of the fifth link 5313e in the vertical direction. The sixth joint unit 5311f is connected to proximal end (lower end) of the second member of the fifth link 5313e.

The sixth joint unit 5311f has a substantially columnar shape and supports, at a distal end side thereof, a proximal end of the fifth link 5313e for rotation around an axis of rotation (sixth axis $O_6$) parallel to the vertical direction. The sixth link 5313f is fixedly connected at a distal end thereof to a proximal end of the sixth joint unit 5311f.

The sixth link 5313f is a bar-like member extending in the vertical direction and is fixedly connected at a proximal end thereof to an upper face of the base unit 5315.

The first joint unit 5311a to sixth joint unit 5311f have movable ranges suitably set such that the microscope unit 5303 can make a desired movement. Consequently, in the arm unit 5309 having the configuration described above, a movement of totaling six degrees of freedom including three degrees of freedom for translation and three degrees of freedom for rotation can be implemented with regard to a movement of the microscope unit 5303. By configuring the arm unit 5309 such that six degrees of freedom are implemented for movements of the microscope unit 5303 in this manner, the position and the posture of the microscope unit 5303 can be controlled freely within the movable range of the arm unit 5309. Accordingly, it is possible to observe a surgical region from every angle, and surgery can be executed more smoothly.

It is to be noted that the configuration of the arm unit 5309 as illustrated is an example at all, and the number and shape (length) of the links including the arm unit 5309 and the number, location, direction of the axis of rotation and so forth of the joint units may be designed suitably such that desired degrees of freedom can be implemented. For example, in order to freely move the microscope unit 5303, preferably the arm unit 5309 is configured so as to have six degrees of freedom as described above. However, the arm unit 5309 may also be configured so as to have much greater degree of freedom (namely, redundant degree of freedom). In the arm unit 5309, where a redundant degree of freedom exists, it is possible to change the posture of the arm unit 5309 in a state in which the position and the posture of the microscope unit 5303 are fixed. Accordingly, control can be implemented which is higher in convenience to the surgeon such as to control the posture of the arm unit 5309 such that, for example, the arm unit 5309 does not interfere with the field of view of the surgeon who watches the display apparatus 5319.

Here, an actuator in which a driving mechanism such as a motor, an encoder which detects an angle of rotation at each joint unit and so forth are incorporated may be provided for each of the first joint unit 5311a to sixth joint unit 5311f. Then, by suitably controlling driving of the actuators provided in the first joint unit 5311a to sixth joint unit 5311f by the control apparatus 5317, the posture of the arm unit 5309, namely, the position and the posture of the microscope unit 5303, can be controlled. Specifically, the control apparatus 5317 can comprehend the posture of the arm unit 5309 at present and the position and the posture of the microscope unit 5303 at present on the basis of information regarding the angle of rotation of the joint units detected by the encoders. The control apparatus 5317 uses the comprehended information to calculate a control value (for example, an angle of rotation, torque to be generated, or the like) for each joint unit with which a movement of the microscope unit 5303 in accordance with an operation input from the user is implemented. Accordingly the control apparatus 5317 drives driving mechanism of each joint unit in accordance with the control value. It is to be noted that, in this case, the control method of the arm unit 5309 by the control apparatus 5317 is not limited, and various known control methods such as force control or position control may be applied.

For example, when the surgeon performs operation inputting suitably through an input apparatus not illustrated, driving of the arm unit 5309 may be controlled suitably in response to the operation input by the control apparatus 5317 to control the position and the posture of the microscope unit 5303. By this control, it is possible to support, after the microscope unit 5303 is moved from an arbitrary position to a different arbitrary position, the microscope unit 5303 fixedly at the position after the movement. It is to be noted that, as the input apparatus, preferably an input apparatus is applied which can be operated by the surgeon even if the surgeon has a surgical tool in its hand such as, for example, a foot switch taking the convenience to the surgeon into consideration. Further, operation inputting may be performed in a contactless fashion on the basis of gesture detection or line-of-sight detection in which a wearable device or a camera which is provided in the operating room is used. This makes it possible even for a user who belongs to a clean area to operate an apparatus belonging to an unclean area with a high degree of freedom. In addition, the arm unit 5309 may be operated in a so-called master-slave fashion. In this case, the arm unit 5309 may be remotely controlled by the user through an input apparatus which is placed at a place remote from the operating room.

Further, where force control is applied, the control apparatus 5317 may perform so-called power-assisted control to drive the actuators of the first joint unit 5311*a* to sixth joint unit 5311*f* such that the arm unit 5309 may receive external force by the user and move smoothly following the external force. With this arrangement, when the user directly moves the position of the microscope unit 5303 while holding the microscope unit 5303, the microscope unit 5303 with comparatively weak force. Accordingly, it becomes possible for the user to move the microscope unit 5303 more intuitively by a simpler and easier operation, and the convenience to the user can be improved.

Further, driving of the arm unit 5309 may be controlled such that the arm unit 5309 performs a pivot movement. Here, the pivot movement here is a motion for moving the microscope unit 5303 such that the direction of the optical axis of the microscope unit 5303 is kept toward a predetermined point (hereinafter referred to as pivot point) in a space. Since the pivot movement makes it possible to observe the same observation position from various directions, more detailed observation of an affected area becomes possible. It is to be noted that, where the microscope unit 5303 is configured such that the focal distance thereof is fixed, preferably the pivot movement is performed in a state in which the distance between the microscope unit 5303 and the pivot point is fixed. In this case, the distance between the microscope unit 5303 and the pivot point is only required to be adjusted to a fixed focal distance of the microscope unit 5303 in advance. By the configuration just described, the microscope unit 5303 comes to move on a hemispherical plane (schematically illustrated in FIG. 30) having a diameter corresponding to the focal distance centered at the pivot point, and even if the observation direction is changed, a clear picked up image can be obtained. On the other hand, where the microscope unit 5303 is configured such that the focal distance thereof is adjustable, the pivot movement may be performed in a state in which the distance between the microscope unit 5303 and the pivot point is variable. In this case, for example, the control apparatus 5317 may calculate the distance between the microscope unit 5303 and the pivot point on the basis of information regarding the angles of rotation of the joint units detected by the encoders and automatically adjust the focal distance of the microscope unit 5303 on the basis of a result of the calculation. Alternatively, where the microscope unit 5303 includes an AF function, adjustment of the focal distance may be performed automatically by the AF function every time the changing in distance caused by the pivot movement between the microscope unit 5303 and the pivot point.

Further, each of the first joint unit 5311*a* to sixth joint unit 5311*f* may be provided with a brake for constraining the rotation of the first joint unit 5311*a* to sixth joint unit 5311*f*. Operation of the brake may be controlled by the control apparatus 5317. For example, if it is intended to fix the position and the posture of the microscope unit 5303, then the control apparatus 5317 renders the brakes of the joint units operative. Consequently, even if the actuators are not driven, the posture of the arm unit 5309, namely, the position and posture of the microscope unit 5303, can be fixed, and therefore, the power consumption can be reduced. In a case where it is intended to move the position and the posture of the microscope unit 5303, the control apparatus 5317 is only required to release the brakes of the joint units and drive the actuators in accordance with a predetermined control method.

Such operation of the brakes may be performed in response to an operation input by the user through the operation unit 5307 described hereinabove. In a case where the user intends to move the position and the posture of the microscope unit 5303, the user would operate the operation unit 5307 to release the brakes of the joint units. Consequently, the operation mode of the arm unit 5309 changes to a mode in which rotation of the joint units can be performed freely (all-free mode). On the other hand, if the user intends to fix the position and the posture of the microscope unit 5303, then the user would operate the operation unit 5307 to render the brakes of the joint units operative. Consequently, the operation mode of the arm unit 5309 changes to a mode in which rotation of the joint units is constrained (fixed mode).

The control apparatus 5317 integrally controls operation of the microscopic surgery system 5300 by controlling operation of the microscope apparatus 5301 and the display apparatus 5319. For example, the control apparatus 5317 renders the actuators of the first joint unit 5311*a* to sixth joint unit 5311*f* operative in accordance with a predetermined control method to control driving of the arm unit 5309. Further, for example, the control apparatus 5317 controls operation of the brakes of the first joint unit 5311*a* to sixth joint unit 5311*f* to change the operation mode of the arm unit 5309. Further, for example, the control apparatus 5317 performs various signal processes for an image signal acquired by the imaging unit of the microscope unit 5303 of the microscope apparatus 5301 to generate image data for display and controls the display apparatus 5319 to display the generated image data. As the signal processes, various known signal processes such as, for example, a development process (demosaic process), an image quality improving process (a bandwidth enhancement process, a super-resolution process, a noise reduction (NR) process, an image stabilization process, and/or the like) and/or an enlargement process (namely, an electronic zooming process) may be performed.

It is to be noted that communication between the control apparatus 5317 and the microscope unit 5303 and communication between the control apparatus 5317 and the first joint unit 5311*a* to sixth joint unit 5311*f* may be wired communication or wireless communication. Where wired communication is applied, communication by an electric signal may be performed or optical communication may be performed. In this case, a cable for transmission used for wired communication may be configured as an electric signal cable, an optical fiber or a composite cable of them in response to an applied communication method. On the other hand, where wireless communication is applied, since there is no necessity to lay a transmission cable in the operating room, such a situation that movement of medical staff in the operating room is disturbed by a transmission cable can be eliminated.

The control apparatus 5317 may be a processor such as a central processing unit (CPU) or a graphics processing unit (GPU), or a microcomputer, a control board, or the like in which a processor and a storage element such as a memory are incorporated. The various functions described hereinabove can be implemented by the processor of the control apparatus 5317 operating in accordance with a predetermined program. It is to be noted that, in the example illustrated, the control apparatus 5317 is provided as an apparatus separate from the microscope apparatus 5301. However, the control apparatus 5317 may be installed in the inside of the base unit 5315 of the microscope apparatus 5301 and configured integrally with the microscope apparatus 5301. The control apparatus 5317 may also include a plurality of apparatus. For example, microcomputers, control boards or the like may be disposed in the microscope unit 5303 and the first joint unit 5311a to sixth joint unit 5311f of the arm unit 5309 and connected for communication with each other to implement functions similar to those of the control apparatus 5317.

The display apparatus 5319 is provided in the operating room and displays an image corresponding to image data generated by the control apparatus 5317 under the control of the control apparatus 5317. In other words, an image of a surgical region picked up by the microscope unit 5303 is displayed on the display apparatus 5319. Note that the display apparatus 5319 may display, in place of or in addition to an image of a surgical region, for example, various kinds of information relating to the surgery such as physical information of a patient or information regarding a surgical procedure of the surgery. In this case, the display of the display apparatus 5319 may be switched suitably in response to an operation by the user. Alternatively, a plurality of such display apparatus 5319 may also be provided such that an image of a surgical region or various kinds of information relating to the surgery may individually be displayed on the plurality of display apparatus 5319. It is to be noted that, as the display apparatus 5319, various known display apparatus such as a liquid crystal display apparatus or an electro luminescence (EL) display apparatus may be applied.

FIG. 31 is a view illustrating a state of surgery in which the microscopic surgery system 5300 illustrated in FIG. 30 is used. FIG. 31 schematically illustrates a state in which a surgeon 5321 uses the microscopic surgery system 5300 to perform surgery for a patient 5325 on a patient bed 5323. It is to be noted that, in FIG. 31, for simplified illustration, the control apparatus 5317 from among the components of the microscopic surgery system 5300 is omitted and the microscope apparatus 5301 is illustrated in a simplified form.

As illustrated in FIG. 31, upon surgery, using the microscopic surgery system 5300, an image of a surgical region picked up by the microscope apparatus 5301 is displayed in an enlarged scale on the display apparatus 5319 installed on a wall face of the operating room. The display apparatus 5319 is installed at a position opposing to the surgeon 5321, and the surgeon 5321 would perform various treatments for the surgical region such as, for example, resection of the affected area while observing a state of the surgical region from a video displayed on the display apparatus 5319.

An example of the microscopic surgery system 5300 to which the technology according to an embodiment of the present disclosure can be applied has been described. It is to be noted here that, while the microscopic surgery system 5300 is described as an example, the system to which the technology according to an embodiment of the present disclosure can be applied is not limited to this example. For example, the microscope apparatus 5301 may also function as a support arm apparatus which supports, at a distal end thereof, a different observation apparatus or some other surgical tool in place of the microscope unit 5303. As the other observation apparatus, for example, an endoscope may be applied. Further, as the different surgical tool, forceps, tweezers, a pneumoperitoneum tube for pneumoperitoneum or an energy device for performing incision of a tissue or sealing of a blood vessel by cautery and so forth can be applied. By supporting any of such an observation apparatus and surgical tools as just described by the supporting apparatus, the position of them can be fixed with a high degree of stability in comparison with that in an alternative case in which they are supported by hands of medical staff. Accordingly, the burden on the medical staff can be reduced. The technology according to an embodiment of the present disclosure may be applied to a support arm apparatus which supports such a component as described above other than the microscopic unit.

6. Conclusion

As described above, according to the embodiments of the present disclosure, a medical system is provided which includes a light source configured to irradiate a subject inside a living organism, an imaging unit configured to image the subject coaxially with an optical axis of the light source, and a control unit configured to control the light source and the imaging unit, the control unit performing control so that a signal compliant with high-dynamic range standards is output by adjusting gradation for a first image signal acquired by the imaging unit. According to such a configuration, in a case where an image is caused to be displayed at an HDR monitor on the basis of an HDR image, it is possible to reduce glare to be felt by a user for an output image by the HDR monitor.

The preferred embodiment of the present disclosure has been described above with reference to the accompanying drawings, whilst the technical scope of the present disclosure is not limited to the above examples. A person skilled in the art may find various alterations and modifications within the scope of the appended claims, and it should be understood that they will naturally come under the technical scope of the present disclosure.

For example, it is possible to create a program for causing the hardware such as CPU, ROM and RAM incorporated in the computer to execute functions equivalent to those of the control unit 110 as described above. In addition, a computer-readable recording medium on which the program is recorded can also be provided.

For example, as described above, a case is assumed where a second image signal having a first dynamic range compliant with high-dynamic range standards is generated by the gradation converting unit 22 on the basis of the HDR image (first image signal) obtained by the HDR image generating unit 21. In such a case, the control unit 20 may automatically switch image signals to be output. That is, the control unit 20 may perform control so that the second image signal is output to the HDR display unit 30-1 in a case where a maximum value of a pixel signal included in the first image signal is greater than a predetermined value, and the first image signal is output to the HDR display unit 30-1 in a case where the maximum value of the pixel signal included in the first image signal is equal to or less than the predetermined value.

Further, the control unit 20 may perform control so that the first image signal and the second image signal are displayed on the same screen of the HDR display unit 30-1. By this means, the user can watch two images having different dynamic ranges at the same time.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the technical scope of the present disclosure may also be configured as below.

(1)

A medical system including:

a light source configured to irradiate a subject inside a living organism;

an imaging unit configured to image the subject coaxially with an optical axis of the light source; and a control unit configured to control the light source and the imaging unit, in which the control unit performs control so that a signal compliant with high-dynamic range standards is output by adjusting gradation for a first image signal acquired by the imaging unit.

(2)

The medical system according to (1), in which the control unit performs control to adjust gradation of the first image signal so that all brightness values of pixel signals included in the first image signal become equal to or less than a first brightness value.

(3)

The medical system according to (2), in which the control unit performs control to adjust gradation for a pixel signal for which a brightness value is greater than a second brightness value so that the brightness value becomes equal to or less than the first brightness value, and performs control so as not to adjust gradation for a pixel signal for which a brightness value is equal to or less than the second brightness value, among the first image signal.

(4)

The medical system according to (1), in which the control unit performs control to determine a first region on the basis of a result of object recognition for the first image signal, performs control to adjust gradation of a pixel signal included in the first region, and performs control so as not to adjust gradation of a pixel signal included in a region other than the first region.

(5)

The medical system according to (4), in which the control unit specifies a second region including a mask, a surgical tool, gauze or a body tissue in the object recognition and determines the first region on the basis of the second region.

(6)

The medical system according to (1), in which the control unit performs control to adjust gradation for a pixel signal of a specific color, and performs control so as not to adjust gradation for pixel signals of other colors, among the first image signal.

(7)

The medical system according to (1), in which the control unit performs control to adjust gradation for the first image signal on the basis of a pixel for which brightness is greater than a second brightness value in the first image signal.

(8)

The medical system according to (7), in which the control unit performs control to determine a first brightness value on the basis of the number of pixels for which brightness is greater than the second brightness value in the first image signal and adjust gradation so that brightness values of all pixel signals of the first image signal become equal to or less than the first brightness value.

(9)

The medical system according to (7), in which the control unit performs control to make brightness of a pixel signal for which brightness is smaller than a third brightness value in the first image signal, greater in a case where the number of pixels for which brightness is greater than the second brightness value in the first image signal is larger than a predetermined number.

(10)

The medical system according to (9), in which the control unit performs control to make brightness greater using a same adjustment amount for pixel signals for which brightness is smaller than the third brightness value.

(11)

The medical system according to (1), in which the control unit determines a second period during which a brightness value of the first image signal is maintained at brightness corresponding to a value included in a predetermined range in accordance with a first period during which the brightness value of the first image signal indicates a value within the predetermined range.

(12)

The medical system according to (1), in which the control unit performs control to determine a degree of adjustment of gradation or a region in which gradation is to be adjusted on the basis of an additional value or an average value of brightness of respective pixel signals constituting the first image signal, and performs control to adjust gradation for the first image signal on the basis of the degree or the region.

(13)

The medical system according to (12), in which the control unit performs control to adjust gradation for the first image signal on the basis of information regarding brightness designated by a user or observation mode information designated by the user.

(14)

The medical system according to (13), in which the information regarding brightness is a maximum brightness value of an image signal, a minimum brightness value of an image signal or an adjustment rate of gradation of an image signal.

(15)

The medical system according to (13), in which the observation mode is a special light observation mode or a normal light mode.

(16)

The medical system according to (1), in which the control unit performs control to adjust gradation for the first image signal on the basis of brightness setting information of a display unit.

(17)

A medical apparatus including:

a control unit configured to perform control to image a subject inside a living organism to acquire a first image signal, generate a second image signal having a first dynamic range compliant with high-dynamic range standards on the basis of the first image signal, generate a third image signal for which a difference between a maximum value of brightness and a minimum value of brightness is smaller than the first dynamic range on the basis of the first image signal, and output the second image signal or the third image signal.

(18)

A medical apparatus including:

a control unit configured to control a light source which irradiates a subject inside a living organism and an imaging unit which images the subject coaxially with an optical axis of the light source, in which the control unit performs control to output a signal compliant with high-dynamic range standards by adjusting gradation for a first image signal acquired by the imaging unit.

(19)

A control method including:

controlling a light source which irradiates a subject inside a living organism and an imaging unit which images the subject coaxially with an optical axis of the light source, and performing control to output a signal compliant with high-dynamic range standards by adjusting gradation for a first image signal acquired by the imaging unit.

(20)

The medical system according to (1), in which the control unit performs control to output a second image signal having a first dynamic range compliant with high-dynamic range standards, which is generated on the basis of the first image signal in a case where a maximum value of a pixel signal included in the first image signal is greater than a predetermined value, and performs control to output the first image signal in a case where the maximum value is equal to or less than the predetermined value.

(21)

The medical system according to (1), in which the control unit performs control to display the first image signal and a second image signal having a first dynamic range compliant with high-dynamic range standards, which is generated on the basis of the first image signal, on a same screen of a display unit.

(22)

The medical system according to (1), in which the medical system is an endoscopic system or a microscopic system.

REFERENCE SIGNS LIST

10 Imaging unit
20 Control unit
21 HDR image generating unit
22 Gradation converting unit
23 Brightness input unit
24 Object recognizing unit
25 High-brightness area calculating unit
26 Brightness average value calculating unit
30-1 HDR display unit
30-2 SDR display unit
40 SDR recording unit

The invention claimed is:

1. A medical system comprising:
a light source configured to irradiate a subject inside a living organism;
imaging circuitry configured to image the subject coaxially with an optical axis of the light source; and
control circuitry configured to:
control the light source and the imaging circuitry, so that a signal compliant with high-dynamic range standards is output by adjusting gradation for a first image signal acquired by the imaging circuitry,
determine a first region in the first image signal based on object recognition, on condition that the object is a first type of object, the control circuitry is configured to adjust gradation of the pixel signal of the first region and not adjust gradation of the pixel signal in a region of than the first region, and on condition that the object is a second type of object, different from the first type of object, the control circuitry is configured to not adjust gradation of the pixel signal of the first region and adjust gradation of the pixel signal in the region of than the first region.

2. The medical system according to claim 1,
wherein circuitry is configured to adjust gradation of the first image signal so that all brightness values of pixel signals included in the the first image signal become equal to or less than a first brightness value.

3. The medical system according to claim 2,
wherein the control circuitry is configured to
adjust gradation for a pixel signal for which a brightness value is greater than a second brightness value so that the brightness value becomes equal to or less than the first brightness value, and
not to adjust gradation for a pixel signal for which a brightness value is equal to or less than the second brightness value, among the first image signal.

4. The medical system according to claim 1, wherein the control circuitry is configured to specify a second object including a mask, a surgical tool, gauze or a body tissue in the object recognition and determines the region other than the first region on a basis of the second object.

5. The medical system according to claim 1,
wherein the control circuitry is configured to adjust gradation for a pixel signal of a specific color, and
not to adjust gradation for pixel signals of other colors, among the first image signal.

6. The medical system according to claim 1,
wherein the control circuitry is configured to adjust gradation for the first image signal on a basis of a pixel for which brightness is greater than a second brightness value in the first image signal.

7. The medical system according to claim 6,
wherein the control circuitry is configured to determine a first brightness value on a basis of a number of pixels for which brightness is greater than the second brightness value in the first image signal and adjust gradation so that brightness values of all pixel signals of the first image signal become equal to or less than the first brightness value.

8. The medical system according to claim 6,
wherein the control circuitry is configured to make brightness of a pixel signal for which brightness is smaller than a third brightness value in the first image signal, greater in a case where a number of pixels for which brightness is greater than the second brightness value in the first image signal is larger than a predetermined number.

9. The medical system according to claim 8,
wherein the control circuitry is configured to make brightness greater using a same adjustment amount for pixel signals for which brightness is smaller than the third brightness value.

10. The medical system according to claim 1,
wherein the control circuitry is configured to determine a second period during which a brightness value of the first image signal is maintained at brightness corresponding to a value included in a predetermined range in accordance with a first period during which the brightness value of the first image signal indicates a value within the predetermined range.

11. The medical system according to claim 1,
wherein the control circuitry is configured to determine a degree of adjustment of gradation or a region in which gradation is to be adjusted on a basis of an additional value or an average value of brightness of respective pixel signals constituting the first image signal, and
to adjust gradation for the first image signal on a basis of the degree or the region.

12. The medical system according to claim 11,
wherein the control circuitry is configured to adjust gradation for the first image signal on a basis of information regarding brightness designated by a user or observation mode information designated by the user.

13. The medical system according to claim 12,
wherein the information regarding brightness is a maximum brightness value of an image signal, a minimum brightness value of an image signal or an adjustment rate of gradation of an image signal.

14. The medical system according to claim 12,
wherein the observation mode is a special light observation mode or a normal light mode.

15. The medical system according to claim 1,
wherein the control circuitry is configured to adjust gradation for the first image signal on a basis of brightness setting information of a display unit.

16. A medical apparatus comprising:
a control circuitry configured to control a light source which irradiates a subject inside a living organism and an imaging circuitry which images the subject coaxially with an optical axis of the light source,
wherein the control circuitry is configured to:
control the light source and the imaging circuitry to output a signal compliant with high-dynamic range standards by adjusting gradation for a first image signal acquired by the imaging circuitry,
determine a first region in the first image signal based on object recognition,
on condition that the object is a first type of object, the control circuitry is configured to adjust gradation of the pixel signal of the first region and not adjust gradation of the pixel signal in a region of than the first region, and
on condition that the object is a second type of object, different from the first type of object, the control circuitry is configured to not adjust gradation of the pixel signal of the first region and adjust gradation of the pixel signal in the region of than the first region.

17. A control method comprising:
controlling a light source which irradiates a subject inside a living organism and an imaging circuitry configured to image the subject coaxially with an optical axis of the light source,
performing control to output a signal compliant with high-dynamic range standards by adjusting gradation for a first image signal acquired by the imaging circuitry,
determining a first region in the first image signal based on object recognition,
on condition that the object is a first type of object, adjusting gradation of the pixel signal of the first region and not adjusting gradation of the pixel signal in a region of than the first region, and
on condition that the object is a second type of object, different from the first type of object, not adjusting gradation of the pixel signal of the first region and adjusting gradation of the pixel signal in the region of than the first region.

18. The medical system according to claim 1,
wherein the control circuitry is configured to control to output a second image signal having a first dynamic range compliant with high-dynamic range standards, which is generated on a basis of the first image signal in a case where a maximum value of a pixel signal included in the first image signal is greater than a predetermined value, and control to output the first image signal in a case where the maximum value is equal to or less than the predetermined value.

19. The medical system according to claim 1,
wherein the control circuitry is configured to control to display the first image signal and a second image signal having a first dynamic range compliant with high-dynamic range standards, which is generated on a basis of the first image signal, on a same screen of a display.

20. The medical system according to claim 1,
wherein the medical system is an endoscopic system or a microscopic system.

* * * * *